US010948484B2

(12) United States Patent
Soldo

(10) Patent No.: US 10,948,484 B2
(45) Date of Patent: Mar. 16, 2021

(54) SAMPLE DEPLETION AND ENRICHMENT TO IMPROVE THE QUALITY OF DIAGNOSTIC TEST RESULTS

(71) Applicant: Veravas, Inc., Oakdale, MN (US)

(72) Inventor: Joshua Caine Soldo, Prior Lake, MN (US)

(73) Assignee: Veravas, Inc., Charleston, SC (US)

( * ) Notice: Subject to any disclaimer, the term of this patent is extended or adjusted under 35 U.S.C. 154(b) by 352 days.

(21) Appl. No.: 15/485,100

(22) Filed: Apr. 11, 2017

(65) Prior Publication Data

US 2018/0292394 A1 Oct. 11, 2018
US 2019/0137484 A9 May 9, 2019

Related U.S. Application Data

(60) Provisional application No. 62/321,108, filed on Apr. 11, 2016.

(51) Int. Cl.
*G01N 33/53* (2006.01)
*B01D 15/38* (2006.01)
(Continued)

(52) U.S. Cl.
CPC ..... *G01N 33/5306* (2013.01); *B01D 15/3809* (2013.01); *B01J 20/28009* (2013.01);
(Continued)

(58) Field of Classification Search
CPC ............ G01N 33/5306; B01D 15/3809; B01J 20/3204; B01J 20/28009; B01J 20/3248;
(Continued)

(56) References Cited

U.S. PATENT DOCUMENTS 5,945,345 A * 8/1999 Blatt .................. G01N 33/5306
422/400
7,465,587 B2 * 12/2008 Imrich ................. G01N 33/558
435/287.7
(Continued)

OTHER PUBLICATIONS

Bjerner J, Olsen KH, Bormer OP, Nustad K, Human heterophilic antibodies display specificity for murine IgG subclasses, Clin Biochem, 2005; 38(5): 465-472.
(Continued)

*Primary Examiner* — Shafiqul Haq
(74) *Attorney, Agent, or Firm* — K&L Gates LLP; Louis C. Cullman; David Diamond

(57) ABSTRACT

Magnetic and non-magnetic microparticle binding surfaces for the simple, cost-effective and automatable depletion of sample interferences within the assay blocking threshold and enrichment of biomarkers are provided, as are methods and compositions for their preparation and use. The binding surfaces may comprise non-magnetic, magnetic, paramagnetic, and superparamagnetic microparticles, or combinations thereof. The methods include methods for making microparticulate binding surfaces that consist of binders, binding partners, capture moieties, or combinations thereof for multi-functional sample depletion and enrichment. Specific examples employing antibodies or fragments thereof are provided, as well as strepavidin-coated microparticles and microparticles coupled with capture moieties such as immunoglobulins. Other examples couple ligands, enzymes, and proteins, or other biologicals, polymers and chemicals commonly used in the diagnostic test formulation or design. Further provided are binding surfaces consisting of a plurality of microparticles and methods for making them. Use of the methods and compositions in connection with the depletion and enrichment of a wide variety of interferences and biomarkers is provided, particularly for use in primary (Continued)

blood collection tubes, secondary transfer tubes and challenging sample types such as urine, saliva and stool.

21 Claims, 15 Drawing Sheets

(51) Int. Cl.
    *B01J 20/32*         (2006.01)
    *B01J 20/28*         (2006.01)

(52) U.S. Cl.
    CPC ....... *B01J 20/3204* (2013.01); *B01J 20/3208* (2013.01); *B01J 20/3248* (2013.01); *B01J 20/3265* (2013.01); *B01J 20/3274* (2013.01)

(58) Field of Classification Search
    CPC . B01J 20/3265; B01J 20/3274; B01J 20/3208
    See application file for complete search history.

(56) References Cited

U.S. PATENT DOCUMENTS

| | | |
|---|---|---|
| 8,518,714 B2 | 8/2013 | Soldo et al. |
| 2015/0038355 A1* | 2/2015 | Tan .................. G01N 33/54393 506/9 |

OTHER PUBLICATIONS

Howerton D, Anderson N, Bosse D, Granade S, Westbrook G, Survey Findings from Testing Sites Holding a Certificate of Waiver Under the Clinical Laboratory Improvement Amendments of 1988 and Recommendations for Promoting Quality Testing, MMWR, Recommendations and Reports, Nov. 11, 2005; 54(RR13): 1-25.
Immunoassay Market [Technology (Enzyme, Fluorescent, Chemiluminescence, Radioimmunoassay), Analyzers & Reagents, Applications (Infectious Diseases, Cancer, Endocrinology, Cardiology), End Users (Hospitals, Laboratory, Academics)]—Global Forecast to 2018. Markets And Markets, Oct. 2013; Report Code: BT 1653, http://www.marketsandmarkets.com/Market-Reports/immunoassay-market-436.html.
Boscato LM, Stuart MC, Heterophilic antibodies: a problem for all immunoassays, Clin Chem, 1988; 34(1): 27-33.
Kroll MH, Elin RJ, Interference with clinical laboratory analyses, Clin Chem, 1994; 40(11 Pt 1): 1996-2005.
Kricka LJ, Human Anti-Animal Antibody Interferences in Immunological Assays, Clin Chem, 1999; 45(7): 942-956.
Sztefko K, Interferences in immunoassay, Przegl Lek, 2002; 59(6): 477-480 [Abstract].
Tate J, Ward G, Interferences in Immunoassay, Clin Biochem Rev, 2004; 25(2): 105-120.
Schiettecatte J, Anckaert E, Smitz J, Chapter 3: Interferences in Immunoassays, pp. 45-62, in Advances in Immunoassay Technology, edited by Chiu NHL and Christopoulos TK, InTech (Rijeka, Croatia), Mar. 2012.
Kricka LJ, Interferences in immunoassay—still a threat, Clin Chem, 2000; 46(8 Pt 1): 1037-1038.
Ismail AA, Barth JH, Wrong biochemistry results, BMJ, 2001; 323(7315): 705-706.
Dietrich CG, Stiegler H, Gressner AM, Matern S, [Heterophile antibodies, lack of communication and the diagnostic dilemma], Med Klin (Munich), 2001; 96(9): 539-544 [English abstract].
Levinson SS, Antibody multispecificity in immunoassay interference, Clin Biochem, 1992; 25(2): 77-87.
Ismail AA, Walker PL, Cawood ML, Barth JH, Interference in immunoassay is an underestimated problem, Ann Clin Biochem. 2002; 39(Pt 4): 366-373.
Sturgeon CM, Viljoen A, Analytical error and interference in immunoassay: minimizing risk, Ann Clin Biochem, 2011; 48(Pt 5): 418-432.

Bolstad N, Warren DJ, Nustad K, Heterophilic antibody interference in immunometric assays, Best Pract Res Clin Endocrinol Metab, 2013; 27(5): 647-661.
Sanmartin N, Garcia C, Bugier S, Malfuson JV, Chianea D, Renard C, Vest P, Heterophilic antibodies: be carefull!, Ann Biol Clin (Paris), 2013; 71(4): 475-480.
Yeo KT, Storm CA, Li Y, Jayne JE, Brough T, Quinn-Hall KS, Fitzmaurice TF, Performance of the enhanced Abbott AxSYM cardiac troponin I reagent in patients with heterophilic antibodies, Clin Chim Acta, 2000; 292(1, 2): 13-23.
Kim WJ, Laterza OF, Hock KG, Pierson-Perry JF, Kaminski DM, Mesguich M, Braconnier F, Zimmermann R, Zaninotto M, Plebani M, Hanna A, Cembrowski GS, Scott MG, Performance of a revised cardiac troponin method that minimizes interferences from heterophilic antibodies, Clin Chem, 2002; 48(7): 1028-1034.
Tate JR, Troponin revisited 2008: assay performance, Clin Chem Lab Med, 2008; 46(11): 1489-1500.
Lippi G, Aloe R, Meschi T, Borghi L, Cervellin G, Interference from heterophilic antibodies in troponin testing. Case report and systematic review of the literature, Clin Chim Acta, 2013; 426: 79-84.
Fortgens PH, Omar F, Cardiac troponin T quantitative assay failure as a result of antibody interference, Afr J Lab Med, 2013; 2(1), Art. #23, 3 pages.
Bonetti A, Monica C, Bonaguri C, Gnocchi C, Russo A, Battistelli L, Musiari L, Pastori P, Novarini A, Interference by heterophilic antibodies in immunoassays: wrong increase of myoglobin values, Acta Biomed, 2008; 79(2): 140-143.
Holmes EW, Garbincius J, McKenna KM, Non-linear analytical recovery in the DiaSorin Liaison immunoassay for 25-hydroxy vitamin D, Clin Chim Acta, 2011; 412: 2355-2356.
Cavalier E, Carlisi A, Beckaert AC, Rousselle O, Chapelle JP, Human anti-animal interference in DiaSorin Liaison total 25(OH)—vitamin D assay: towards the end of a strange story?, Clin Chim Acta, 2012; 413: 527-528.
Farrell C, Soldo J, Williams P, Herrmann M, 25-Hydroxyvitmain D testing: challenging the performance of current automated immunoassays, Clin Chem Lab Med, 2012; 50: 1953-1963.
Holmes EW, Garbincius J, McKenna KM, Analytical Variability Among Methods for the Measurement of 25-Hydroxyvitamin D, Am J Clin Pathol, 2013; 140: 550-560.
Farrell CJ, Soldo J, McWhinney B, Bandodkar S, Herrmann M, Impact of assay design on test performance: lessons learned from 25-hydroxyvitamin D, Clin Chem Lab Med, 2014; 52(11): 1579-1587.
Vladutiu AO, Sulewski JM, Pudlak KA, Stull CG, Heterophilic antibodies interfering with radioimmunoassay. A false-positive pregnancy test, JAMA, 1982; 248(19): 2489-2490.
Butler SA, Cole LA, Use of Heterophilic Antibody Blocking Agent (HBT) in Reducing False Positive hCG Results, Clin Chem, 2001; 47(7): 1332-1333.
Webster R, Fahie-Wilson M, Barker P, Chatterjee VK, Halsall DJ, Immunoglobulin interference in serum follicle-stimulating hormone assays: autoimmune and heterophilic antibody interference, Ann Clin Biochem, 2010; 47(Pt 4): 386-389.
Todd DJ, Knowlton N, Amato M, Frank MB, Schur PH, Izmailova ES, Roubenoff R, Shadick NA, Weinblatt ME, Centola M, Lee DM, Erroneous augmentation of multiplex assay measurements in patients with rheumatoid arthritis due to heterophilic binding by serum rheumatoid factor, Arthritis Rheum, 2011; 63(4): 894-903.
Kragstrup TW, Vorup-Jensen T, Deleuran B, Hvid M, A simple set of validation steps identifies and removes false results in a sandwich enzyme-linked immunosorbent assay caused by anti-animal IgG antibodies in plasma from arthritis patients, Springerplus, 2013; 2(1): 263.
DeForge LE, Loyet KM, Delarosa D, Chinn J, Zamanian F, Chuntharapai A, Lee J, Hass P, Wei N, Townsend MJ, Wang J, Wong WL, Evaluation of heterophilic antibody blocking agents in reducing false positive interference in immunoassays for IL, 17AA, IL-17FF, and IL-17AF, J Immunol Methods, 2010; 362(1, 2): 70-81.
Buijs MM, Gorgets JP, Endert E, Interference by antiruthenium antibodies in the Roche thyroid-stimulating hormone assay, Ann Clin Biochem, 2011; 48(Pt 3): 276-281.

(56) References Cited

OTHER PUBLICATIONS

Sapin R, Agin A, Gasser F, Efficacy of a new blocker against anti-ruthenium antibody interference in the Elecsys free triiodothyronine assay, Clin Chem Lab Med, 2007; 45(3): 416-418.

Zaninotto M, Tognon C, Venturini R, Betterle C, Plebani M, Interference in thyroid hormones with Roche immunoassays: an unfinished story, Clin Chem Lab Med, 2014; 52(12): e269-e270.

Kwok JS, Chan IH, Chan MH, Biotin interference on TSH and free thyroid hormone measurement, Pathology, 2012; 44(3): 278-80.

Beltran L, Fahie-Wilson MN, McKenna TJ, Kavanagh L, Smith TP, Serum total prolactin and monomeric prolactin reference intervals determined by precipitation with polyethylene glycol: evaluation and validation on common immunoassay platforms, Clin Chem, 2008; 54(10): 1673-1681.

Lakos G, Interference in antiphospholipid antibody assays, Semin Thromb Hemost, 2012; 38(4): 353-359.

Preissner CM, Dodge LA, O'Kane DJ, Singh RJ, Grebe SKG, Prevalence of Heterophilic Antibody Interference in Eight Automated Tumor Marker Immunoassays, Clin Chem, 2005; 51(1): 208-210.

Vanderstichele H, Stoops E, Vanmechelen E, Jeromin A, Potential sources of interference on Abeta immunoassays in biological samples. Alzheimers Res Ther, 2012; 4(5): 39.

Altinier S, Varagnolo M, Zaninotto M, Boccagni P, Plebani M, Heterophilic antibody interference in a non-endogenous molecule assay: an apparent elevation in the tacrolimus concentration, Clin Chim Acta, 2009; 402(1, 2): 193-195.

Marks V, False-positive immunoassay results: a multicenter survey of erroneous immunoassay results from assays of 74 analytes in 10 donors from 66 laboratories in seven countries, Clin Chem, 2002; 48(11): 2008-2016.

Bolstad N, Warren DJ, Bjerner J, Kravdal G, Schwettmann L, Olsen KH, Rustad P, Nustad K, Heterophilic antibody interference in commercial immunoassays; a screening study using paired native and pre-blocked sera, Clin Chem Lab Med, 2011; 49(12): 2001-2006.

Gorovits B, McNally J, Fiorotti C, Leung S, Protein-based matrix interferences in ligand-binding assays, Bioanalysis, 2014; 6(8): 1131-1140.

Rulander NJ, Cardamone D, Senior M, Snyder PJ, Master SR, Interference From Anti-Streptavidin Antibody, Arch Pathol Lab Med, 2013; 137: 1141-1146.

Wijeratne NG, Doery JC, Lu ZX, Positive and negative interference in immunoassays following biotin ingestion: a pharmacokinetic study,. Pathology, 2012; 44(7): 674-675.

Holm BE, Sandhu N, Tronstrom J, Lydolph M, Trier NH, Houen G, Species cross-reactivity of rheumatoid factors and implications for immunoassays, Scand J Clin Lab Invest, 2015; 75(1): 51-63.

Class 2 Device Recall ADVIA Centaur Systems VitD 100 test, Ready Pack (Z-1656-2014), http://www.accessdata.fda.gov/scripts/cdrh/cfdocs/cfRES/res.cfm?id-%20=126653.

Xu RN, Fan L, Rieser MJ, El-Shourbagy TA, Recent advances in high-throughput quantitative bioanalysis by LC-MS/MS, J Pharm Biomed Anal, 2007; 44(2): 342-355.

Zheng N, Jiang H, Zeng J, Current advances and strategies towards fully automated sample preparation for regulated LC-MS/MS bioanalysis, Bioanalysis, 2014; 6(18): 2441-2459.

Bylda C, Thiele R, Kobold U, Volmer DA, Recent advances in sample preparation techniques to overcome difficulties encountered during quantitative analysis of small molecules from biofluids using LC-MS/MS, Analyst, 2014; 139(10): 2265-2276.

\* cited by examiner

Human Anti-Mouse Antibodies (HAMA)
The immunoassay is protected against potential interferences with HAMA by adding a protection in the tracer of non-specific mouse immunoglobulins. Nevertheless, one cannot assure that there will never be a "false positive" result due to the presence of heterophilic antibodies in a patient sample.

FIG. 1

Limitations of Procedure
1. This product is for use on UniCel DxI Immunoassay Systems only. It is not compatible with Access 2 Immunoassay Systems.
2. The reportable measuring range of the assay is defined as the range from the limit of detection (LoD) to the Calibrator S5 value, 2.00 to approximately 210 ng/mL (5.0 to ~525 nmol/L). Values outside of this range should be reported as < 2.00 ng/mL or > S5 Calibrator value (~210 ng/mL), respectively. Do not dilute patient samples, as this could lead to incorrect Vitamin D results.
3. For assays employing antibodies, the possibility exists for interference by heterophile antibodies in the patient sample. Patients who have been regularly exposed to animals or have received immunotherapy or diagnostic procedures utilizing immunoglobulins or immunoglobulin fragments may produce antibodies, e.g. HAMA, that interfere with immunoassays. Additionally, other heterophile antibodies (e.g. human anti-sheep antibodies) may be present in patient samples.15, 16 Such interfering antibodies may cause erroneous results. Carefully evaluate the results of patients suspected of having these antibodies.
4. Other potential interferences in the patient sample could be present and may cause erroneous results in immunoassays. Some examples that have been documented in literature include rheumatoid factor, endogenous alkaline phosphatase, fibrin, and proteins capable of binding to alkaline phosphatase.17 Carefully evaluate the results of patients suspected of having these types of interferences.
5. The Access 25(OH) Vitamin D Total results should be interpreted in light of the total clinical presentation of the patient. including: symptoms, clinical history, data from additional tests, and

FIG. 2

| Correct Dose | All assay reagents (capture antibody, conjugate, and antigen) are free to bind without steric hindrance, bridging or competition, and results in a correct dose. | Correct Signal (RLU or relative light units) |
|---|---|---|
| Failure Mode 1: HAAA Steric Hindrance | HAAA (i.e. Human anti- bovine, goat. mouse, rabbit, sheep antibodies) binds to the capture antibody and/or conjugate. Subsequent steric hindrance by human IgG and/or IgM prevents binding of the conjugate to the solid phase, or binding of the conjugate or capture antibody to the antigen, and False Low Signal results in a false low dose, or a false negative in a sandwich assay, or false high dose, or a false positive in a competitive assay. | False Low Signal |
| Failure Mode 2: HAAA Bridging | HAAA binds to the Fc, Fab, or other capture antibody epitopes on the solid phase, as well as to similar FC, Fab or other antibody epitopes on the conjugate. Subsequent bridging from excess or non-specific binding of the conjugate by human IgG and/or IgM results in a false high dose, or a false positive in a sandwich assay, or a false low dose, or a false negative in a competitive assay. Bridging is a greater risk for those assays that use the same species of antibody (e.g. murine monoclonal antibodies) for 2 or more of the antibodies used in the assay (i.e. HAMA interference). | False High Signal |
| Failure Mode 3: MASI Bridging | MASI binds to the conjugate scaffold (i.e. BSA, polymer), or binds to the conjugate label (i.e. Human anti-ALP, acridinium ester, ruthenium, or ABEI antibodies). Excess or non-specific binding of the conjugate by human IgG and/or IgM results in bridging and a false high dose, or a false positive in a sandwich assay, and a false low dose, or a false negative in a competitive assay. | False High Signal |
| Failure Mode 4: MASI Steric Hindrance | MASI binds to the conjugate label (e.g. i.e. human anti-ALP, acridinium ester, ruthenium, or ABEI antibodies). Subsequent steric hindrance prevents binding of the conjugate to the solid phase and results in a false low dose, false negative in a sandwich assay, or a false high dose, or false positive in a competitive assay. | False Low Signal |
| Failure Mode 5: MASI Competition | MASI binds to the solid phase anti-tag binding partner (i.e. free biotin to SAv, exogenous fluorescein to anti-fluorescein antibody ) and competes for and occupies available binding binding sites thereby decreasing the binding capacity of the solid phase. Competition prevents binding of the tag labeled False Low Signal antibody or sandwich complex to the solid phase, which results in a false low dose, or a false negative in a sandwich assay, or a false high dose, or a false positive in a competitive assay. | False Low Signal |

FIG. 3

SAMPLE DEPLETION AND ENRICHMENT TO IMPROVE THE QUALITY OF DIAGNOSTIC TEST RESULTS

CROSS-REFERENCE TO RELATED PATENT APPLICATIONS

The present application claims the benefit to U.S. Provisional Patent Application No. 62/321,108, filed on Apr. 11, 2016, the content of which is incorporated herein by reference in its entirety.

FIELD OF INVENTION

The present invention relates to magnetic and non-magnetic microparticulate binding surfaces comprising binders, binding partners, capture moieties and blockers for use to deplete sample interference and interference mechanisms, or enrich biomarkers, prior to the diagnostic test. Particular aspects of the invention relate to microparticulate binding surfaces comprising antibodies or fragments thereof, capture moieties, ligands, enzymes, proteins, and other biologicals, polymers and chemicals commonly used in the diagnostic test formulation or design. Further embodiments of the present invention relate to the use of a plurality of microparticulate binding surfaces, lyophilized microparticles, and the Assay Blocking Threshold in custom primary blood collection tubes and secondary transfer tubes to pre-treat samples prior to the diagnostic test to deplete know sample interferences and interference mechanisms. Additional embodiments of the present invention relate to the use of microparticulate binding surfaces to enrich biomarkers in challenging sample types such as urine, saliva and stool prior to the diagnostic test, or for immunoextraction prior to the diagnostic test. Methods for making and using such supports are provided.

ABBREVIATIONS

ABEI N-(4-aminobutyl)-N-ethylisoluminol
ABT Assay Blocking Threshold
ALP Alkaline phosphatase
BSA Bovine serum albumin
Fab Fragment antibody-binding
Fc Fragment, crystallizable
HAAA Human anti-animal antibody
HAMA Human anti-mouse antibody
HASA Human anti-sheep antibody
IFU Instructions for use
IgG Antibody or immunoglobulin
IgM Immunoglobulin M
IVD In vitro diagnostics
HRP Horse radish peroxidase
LC-MS/MS Liquid chromatography tandem-mass spectrometry
LDT Laboratory developed test
Mab Monoclonal antibody
MASI Manufacture assay specific interference
MFG IVD Manufacturers
PMP Superparamagnetic microparticles
POCT Point-of-care tests
PBCT Primary blood collection tubes
RF Rheumatoid Factor
RLU Relative light units or assay response signal
RUO Research use only
SAv Streptavidin
STT Secondary transfer tubes
TAT Turnaround time
WF Work flow

BACKGROUND

Laboratory testing plays a critical role in health assessment, health care, and ultimately the public's health, and affects persons in every life stage. Almost everyone will experience having one or more laboratory tests conducted during their lifetime. An estimated 7 to 10 billion laboratory tests are performed each year in the United States alone, and laboratory test results influence approximately 70% of medical decisions (2-3).

Interference is a substance present in a patient specimen that can atter the correct value of the result by interfering with antibody binding, or that can increase or decrease assay signal by bridging, steric hindrance, or autoantibody mechanisms (4-9). While it is known that immunoassays are susceptible to interference, the clinical laboratory may still report erroneous results if such results are not recognized and flagged by the instrument (analyser) or laboratory, or if the physician does not notify the laboratory that the patient result does not fit the clinical picture. Erroneous results can occur unexpectedly with any specimen without the practical means to identify upfront such specimens likely to cause problems. The consequence of such interference is that erroneous results can impact patient care, and can lead to unnecessary invasive, diagnostic or therapeutic procedures, or failure to treat a patient with a false negative test result (10-17, 29).

Interference has been reported in numerous clinically and commercially important immunoassays such as cardiac Troponin C, I and T (17-22), myoglobin (23), 25-OH vitamin D total (24, 28, 51), human chorionic gonadotropin (hCG and beta-hCG) (4, 29, 30), serum follicle-stimulating hormone (FSH) (31), rheumatoid arthritis and spondyloarthritis (interleukin-24) (32, 33), IL-17AA, IL-17FF and IL-17AF (34), free triiodothyronine (fT3) and free thyroxine (fT4) (35-37), TSH (35, 38, 51), total and monomeric prolactin (39), antiphospholipid antibody assays (cardiolipin, B2-gylcoprotein) and coagulation assays (lupus anticoagulants) (40), tumor marker assays (41), drug monitoring (tacrolimus) and therapeutic product assays (42, 43, 46), and a variety of additional assays (17-50). In 2014 the FDA issued a Class 2 Recall for the Siemens Centaur BRAHAMS PCT assay, TSH3 Ultra assay, and VitD TOTAL assay due to assay interference (51).

There are many sources of sample specific interference in the clinical laboratory such as sample type (i.e. plasma), carry-over, freeze/thaw, stability, haemolysis, icterus, lipemia, effects of anticoagulants, agar, sample storage, binding proteins, drugs and drug metabolites, and cross-reactivity (9-10). However, heterophilic antibody interference such as human anti-animal antibody (HAAA) and human anti-mouse antibody (HAMA) (4, 6, 12, 16-21, 23, 25, 28, 43, 50), rheumatoid factor (RF) (32, 49), autoantibodies (22, 42), and Manufacture assay specific interference (MASI) (28, 31, 37-38, 45-48, 51) are the most troublesome and problematic as they are difficult to detect and can drastically affect patient management. Studies have been completed to try and determine the prevalence of heterophilic antibody interference, and results range from as low as 0.05% to as high as 80% for a given assay and patient population (4, 6, 14, 19, 21, 32, 34, 44, 45).

Laboratories can troubleshoot and confirm suspected interference in patient specimens using approaches such as dilution recovery, dilution linearity, protein A or protein G affinity chromatography, polyethylene glycol (PEG) protein precipitation, acetonitrile (organic solvent) protein precipitation, immunosubtraction (column-based affinity absorption such as streptavidin-agarose absorption), size exclusion chromatography, pre-incubating the specimen with mouse, goat and/or bovine IgG, or testing the specimen by an alternative assay or technology (8-9, 12, 15, 19, 21-22, 24, 31-33, 43, 47). Laboratories can also use blocking reagents such as Heterophilic Blocking Reagent and Heterophilic Blocking Tubes (Scantibodies), MAK33 (Roche Diagnostics), Immunoglobulin Inhibiting Reagent (Bioreclamation), and Heteroblock (Omega Biologicals) to pre-treat specimens suspect for interference (6, 8-9, 12, 15, 18, 21, 23, 30, 32, 34, 43-45, 49). However, all commercial blocking reagents sold today are research use only (RUO), and therefore they can only be used to troubleshoot patient results not fitting the clinical picture, atypically high or low results (i.e. out of range results), or results recognized and flagged by the test instrument or laboratory. Sample pre-treatment approaches used today impact laboratory workflow (WF) and turnaround time (TAT). Laboratories can only report suspected interference(s) to the physician and recommend testing the specimen by an alternative method.

None of these pre-treatment approaches are simple, cheap, or automatable, nor can they address multiple mechanisms of sample specific interference at the same time. Sample pre-treatment approaches used today impact laboratory workflow (WF) and turnaround time (TAT), and since they alter or change the sample composition (i.e. addition of a liquid or lyophilized blocker reagent, total protein or antibody depletion or absorption after protein precipitation or affinity depletion, etc.), the clinical laboratory cannot report the patient result after such pre-treatment. Laboratories can only report suspected interference(s) to the physician and recommend testing the specimen by a different assay or alternative method (8, 15, 21). Moreover, all commercial blocking reagents sold today are research use only (RUO), and therefore they can only be used to troubleshoot patient results not fitting the clinical picture, atypically high or low results (i.e. out of range results), or results recognized and flagged by the test instrument or laboratory. In order for a laboratory to consider reporting patient results after sample pre-treatment, they must validate a laboratory developed test (LDT) to demonstrate a specific pre-treatment approach does not change the assay performance and the LDT still meets assay MFG claims 33, 39, 43).

While laboratories have approaches to troubleshoot and confirm suspect sample interference, it is best for the assay MFG to design their assays to mitigate such interference as much as possible to minimize the prevalence and magnitude of interference, and to invest the necessary resources in specific protective measures against heterophilic interference (16, 28). The use of antibody Fab fragments, antibodies from different subclasses and species, and new blockers and blocking strategies are some approaches MFG continue to explore (9, 33, 49). MFG do their best to design their assays to mitigate interference such as adding blocking reagents to the conjugate, beads, and/or assay buffer, assay format/design and order of addition (1-step vs. 2-step vs. delayed addition formats), additional incubation steps, incubation time, use of antibody Fab fragments, and/or decreasing sample size (18, 19). However assay interference is still an issue with modern immunoassays (16-17, 28, 37-38, 48-49, 51). MFG are aware of heterophiles and assay specific interference specific to the reagent(s) used in their assay construct and design that may impact the accuracy of results, and they add language to their package inserts or instructions for use (IFU) to acknowledge this immunoassay limitation or weakness.

For example, since Cisbio uses monoclonal antibodies (Mab) in their Renin III Generation assay construct they have added HAMA specific blocker(s) to the tracer (conjugate) to try and mitigate HAMA interference. However, in their package insert they specify that HAMA interference or other heterophilic antibodies in a specific patient specimen may still result in a "false positive" result in their assay (FIG. 1). Although Cisbio has added heterophilic antibody blocker(s) to their assay, they can only add a defined quantity or concentration of such blockers as per their assay validation, Design Control, and Regulatory submission(s) concerning assay formulation, or in other words their assay design and blocking strategy is locked. Any unblocked heterophiles can still interfere in the Cisbio assay and result in a false positive result.

As another example, Beckman Coulter describes two different mechanisms of interference that can impact the results of their Access 25OH Vitamin D Total Assay. Heterophilic antibodies such as HAMA or HAAA can interact or bind to the sheep monoclonal anti-25(OH) vitamin D antibody used in their assay construct, and other potential interferences such as RF, endogenous alkaline ALP, fibrin, and proteins capable of binding to ALP since they use both sheep Mab and ALP in their assay construct. Beckman Coutter's limitations of procedure statement is necessary as even they added blockers to the 25OH Vitamin D Total assay to mitigate known sample interference mechanisms such as HAMA, human anti-sheep antibody (HASA), RF and ALP interference, they can only add a defined concentration of such blockers as per their assay design, validation, Design Control, and Regulatory submission(s) concerning assay formulation (FIG. 2).

Heterophilic antibody interference includes HAAA IgG and/or IgM with specificity or avidity to bovine, goat, mouse, rabbit, and sheep IgG, and RF interference with specificity to the Fc region of antibodies. MASI is associated with assay specific reagents or raw materials used in the assay design or formulation such as the tracer (ABEI, acridinium ester, ALP, HRP, ruthenium), assay specific proteins (BSA, streptavidin), assay tags (biotin, fluorescein), and conjugation spacers/linkers (i.e. NHS-LC, NHS-LC-LC, NHS-PEO$_{(n)}$) used to attach the tracer or tag to the antibody, analyte, carrier protein, or conjugate scaffold. Both HAAA and MASI interference mechanisms can result in falsely decreased or increased assay signal response or RLU (FIG. 3). The failure modes described in FIG. 3 are due to steric hindrance, bridging, or competition mechanisms, and depending on the assay format (sandwich, competitive or delayed capture) assay interference can result in a falsely increased dose, or "false positive", or a falsely decreased dose, or "false negative".

The use of antibody Fab fragments, antibodies from different subclasses and species, and new blockers and blocking strategies are some approaches MFG and assay developers continue to explore. Blocking strategies and reagents used today include BSA, ovalbumin, animal antibodies (bovine, goat, mouse, rabbit, sheep IgG), animal serum (bovine, goat, mouse, rabbit, sheep serum), polyvinylalcohol (PVA), polyvinylpyrrolidone (PVP), surfactants and detergents (Tween 20, Triton X-100, polyethylene glycol (PEG)-based blockers), commercial blockers (i.e. MAK33, HBR, HBR+, IIR), and inactivated assay components (inactivated ALP, HRP, or inactive analogues of isoluminol, acridinium ester, ruthenium). Other approaches used today to reduce assay interference include addition of blocking reagents to the conjugate, beads, and/or assay buffer, sample size, order of addition, delayed addition, washes (i.e. 1-step vs. 2-step), incubation time with blocker(s), and use of assay buffer.

The concept that MFG have designed their assays to mitigate known mechanisms of heterophilic antibody and assay-specific interference regardless of the titer (concentration), avidity (attraction or affinity to the assay reagents), and mechanism(s) can be referred to as the Assay Blocking Threshold, or ABT (FIG. 4) and is defined by the following assay development and design factors, a) the specific type of blocker(s) used in the assay; b) the concentration or quantity of blocker(s) used in the assay; c) which assay reagents (solid phase, conjugate/tracer, assay buffers, pre-treatment buffer, etc.) have blocker(s) in their respective diluents; d) how long the blockers incubate with the sample; e) the sample volume; f) the assay reagent volumes and sample dilution factor during the assay; g) the assay steps, number of washes, and sequence of washes (i.e. 1-step, 2-step, etc.); h) if an assay buffer(s) is used to dilute and/or pre-treat the sample and store blocker(s); i) the order of addition (sample pre-treatment, delayed addition/Piggy Back, etc.). The use of antibody fragments (Fab, F(ab')2, Fc), antibodies from different subclasses and species, including chimeric antibodies, can also be components of the ABT. All ABT factors combined define the final assay formulation and format. However, patient specimens with a titer, avidity, and/or mechanism of interference the falls outside the assay blocking threshold can still interfere in the assay and result in false high or false low results depending on the mechanism(s) of interference and assay format.

MFG have a very challenging task of formulating and designing an assay that not only meets the analytical and clinical Design Goals and Design Inputs required for Regulatory assay clearance (510(k)) or approval (PMA) by the FDA, or acceptance by clinical laboratories inside and outside the U.S.A. (i.e. CE Mark), but that also can successfully block and mitigate specimen-specific interference regardless of the titer, avidity and/or mechanisms of such interference. Even those assays that were previously believed to be free of interference can suddenly experience unforeseen or non-obvious interference in the laboratory. Examples include the Siemens Centaur BRAHAMS PCT assay, TSH3 Ultra assay, and VitD TOTAL assay (51), and the Roche Elecsys Vitamin D assay (28). In the case of the Siemens Healthcare assays, a monoclonal anti-fluorescein antibody bead (solid phase) is utilized to bind a fluorescein-labeled target. If the patient specimen happens to contain high levels of exogenous fluorescein (i.e. blood drawn from a patient treated with fluorescein without allowing clearance of fluorescein), they can compete for the solid phase anti-fluorescein antibody and result in a falsely suppressed assay signal. Therefore, patient specimens with a titer, avidity, and/or mechanism of interference the falls outside the ABT can still interfere in the assay and result in false high or false low results depending on the mechanism(s) of interference and assay format. Even those assays that were previously believed to be free of interference can suddenly experience unforeseen or non-obvious interference in the laboratory. In 2014 the FDA issued a Class 2 Recall for the Siemens Centaur BRAHAMS PCT assay, TSH3 Ultra assay, and VitD TOTAL assay due to assay interference. While studies have demonstrated a prevalence of heterophilic interference from as low as 0.05% to as high as 80%, heterophilic antibodies (HAAA), rheumatoid factor (RF), and Manufacture assay specific interference (MASI) are the most troublesome and problematic mechanisms of interference as they are difficult to detect and can drastically affect patient management. MFG must design their assays to mitigate known mechanisms of heterophilic antibody and assay-specific interference regardless of the titer (concentration), avidity (attraction or affinity to the assay reagents), and mechanism(s).

In a sandwich assay, the conjugate antibody, protein or binding moiety is labeled with the Manufacturer/platform-specific chemiluminescent substrate such as acridinium, isoluminol or ruthenium, or with a chemiluminescent enzymatic protein such as ALP or HRP, and the capture antibody, protein or binding moiety is coated to the microparticles or free in solution for subsequent capture by the microparticulate binding surface. For example, Abbott, IDS, DiaSorin, Roche and Siemens use small chemiluminescent molecules in their conjugates (acridinium ester, ABEI, ruthenium), while Beckman Coulter and Ortho Clinical Diagnostics use large proteins (ALP, HRP). In the absence of HAAA, both the capture antibody and conjugate are free to bind the antigen and form a sandwich. In double antibody sandwich assays the amount of antigen present in the patient sample is directly proportional to the amount of relative light units (RLU) or signal detected by the system, and the assay dose response is directly proportional to the assay signal response, or number (moles) of sandwiches formed and captured on the microparticulate binding surface and still bound to the microparticles after the final wash(es) and substrate addition to generate a signal response (FIG. 5).

If there is HAAA present in the specimen, heterophilic antibodies can interact and bind to the conjugate and/or capture antibody and sterically block or hinder the ability of either antibody to bind to the antigen or to form the sandwich. For example, human IgG and/or IgM with specificity and avidity to the capture antibody, conjugate, or both, such as HAMA specific to a subclass of murine monoclonal immunoglobulins such as IgG1, IgG2a, IgG2b and IgG3 commonly used in assays today (50), can sterically crowd the solid phase antibody and/or conjugate so that they cannot freely form a sandwich with the antigen. Since assay dose response is directly proportional to the number of sandwiches formed or captured on the microparticulate binding surface, a failure to form and/or capture the correct number of sandwiches will result in suppressed assay signal and may result in an erroneously low result (FIG. 6).

Bridging or signal amplification is the other primary mechanism of HAAA whereby human IgG and/or IgM bind to the capture antibody and conjugate forming an antigen independent sandwich. In bridging, HAAA mimics the antigen resulting in non-specific capture of the conjugate on the microparticulate binding surface, or binds the conjugate to the capture antibody regardless if either antibody has captured the antigen. This form of HAAA is a greater risk for those assays that use two or more of the same species of antibody in the assay. As assay dose response is directly proportional to the number of sandwiches formed or captured on the solid phase, bridging will result in elevated assay signal and may result in an erroneously high result, or a false positive. This is the classic "HAMA" interference mechanism that can be antibody Fc specific, Fab specific, or animal species or IgG subclass specific (FIG. 7). Since typical procedures and conjugation chemistries used to attach or bind antibodies to the microparticulate binding surface do not necessarily orientate the antibody on the surface it is likely antibody can lay down on the surface in a multitude of different orientations including Fc down, Fc up, and a mixture or orientations. Fc up orientation is most susceptible to Fc-specific or RF interference as demonstrated in FIG. 7C.

Competitive assay formats are commonly used by MFG to measure small molecules or low molecular weight analytes such as endocrinology markers, steroids, and drugs of abuse. In a competitive assay the conjugate is the antigen (or analogue thereof) covalently attached to the MFG/platform-specific chemiluminescent substrate such as ABEI, acridinium, isoluminol or ruthenium, or the antigen is covalently attached to a chemiluminescent enzymatic protein such as ALP or HRP. In the absence of interference, both the antigen and conjugate are free to bind to and compete for the capture antibody, protein or binding moiety binding sites or epitopes. In competitive inhibition assays an inverse relationship exists between the amount of antigen present in the patient sample and the amount of RLU or signal detected by the system. Since the capture antibody is limiting and is not in molar excess to the antigen or conjugate, assay signal dose is inversely proportional to the assay signal response, or to the number (moles) of conjugate captured by the capture antibody and still bound to solid phase after the final wash and substrate addition The two most common competitive assay formats used today are a direct or true competition, or a backfill or Piggy Back competition (FIG. 8).

However, if there is HAAA interference in the specimen, heterophilic antibodies such as Human IgG and/or IgM (anti-bovine, goat, mouse, rabbit, sheep antibodies) can bind to the capture antibody, conjugate, or both, and sterically crowd the capture antibody and/or conjugte so that they cannot freely bind to eachother. HAAA interference is more problematic with larger molecular weight tracers such as ALP and HRP. As assay dose response is indirectly proportional to the number of conjugates captured on the solid phase, a failure to capture the correct number of conjugates will result in suppressed assay signal and may result in an erroneously high result (FIG. 9). Incorrect competitive assay binding due to HAAA bridging whereby human IgG and/or IgM binds to the conjugate, or to the conjugate scaffold and/or linker, independent of antigen competition or concentration can result in non-specific binding of the conjugate by the capture antibody. As assay dose response is indirectly proportional to the number of conjugates captured on the solid phase, bridging will result in elevated assay signal and an erroneously low result. For example, human anti-ALP IgM can bind to ALP conjugate captured by the capture antibody as well as additional ALP conjugates (FIG. 10).

A delayed capture assay format is a homogeneous solution-based sandwich binding between a tag labeled capture antibody (i.e. a biotin or fluorescein labeled antibody), conjugate (i.e. labeled with a chemiluminescent molecule or enzyme) and the antigen, or homogeneous solution-base competitive binding of antigen and tag labeled antigen (i.e. antigen conjugated to biotin or fluorescein) to the conjugate. In the absence of sample specific endogenous interference, or MASI, such as free biotin or free fluorescein from the diet, supplementation, medicine or medical therapy, the microparticle binding protein [i.e. streptavidin (SAv), anti-fluorescein antibody] is free to bind the tag labeled sandwich complex, or the microparticle binding protein is free to bind the tag labeled antigen, whether it is free or bound to the conjugate. In delayed capture assays the capture antibody is labeled with a tag (i.e. biotin, fluorescein) for subsequent capture by an anti-tag solid phase and assay signal is dependent on successful capture of the tag-labeled capture antibody by the anti-tag solid phase. Assay dose is directly proportional to signal response in the sandwich delayed capture assay format, but dose will be inversely proportional to signal response in the competitive delayed capture assay format (FIG. 11).

If there is MASI present in the patient specimen such as biotin or fluorescene from the patient's diet, supplements, medication, or medical therapy, these interfering substances can bind to the microparticulate binding protein if said protein has high specificity or cross-reactivity to the interfering substance (FIG. 12). For example, if the patient was eating a diet high in biotin (also known as vitamin H or coaenzyme R), or was taking nutritional supplements and/or medication containing high levels of biotin, their blood may also contain high levels of biotin. Such a patient, if tested by an assay format employing a delayed SAv microparticulate binding surface could result in erroneously high or low results if free endogenous biotin in the patient sample competes for the SAv biotin binding sites, or if the free biotin decreases total SAv solid phase biotin binding capacity. If such intererence occurs the SAv will not be able to freely bind the biotin labeled sandwich complex or the biotin labeled antigen resulting is suppressed assay signal (28, 38). As another example, patient samples containing fluorescein (i.e. fluorescein angiography eye tests use a special dye and camera to look at blood flow in the retina and choroid) could result in erroneous results if tested by an assay employing a delayed anti-fluorescein antibody solid phase capture assay format (51).

Heterophilic antibody interference is an inherent weakness of immunoassays as compared against liquid chromatography tandem-mass spectrometry (LC-MS/MS) and molecular diagnostic methods that mitigate protein based interference due to organic extraction (protein precipitation) and solid phase extraction (SPE). Since LC-MS/MS and Molecular Diagnostics offer superior specificity and sensitivity compared to immunoassays, and with recent advancements in SPE, column switching, and analysis automation, the throughput of these new technologies can now rival some of the fully automated immunoassay analyzers (52-54). In fact, many clinical laboratories have started to implement LC-MS/MS for routine testing of small molecules (i.e. testosterone, estradiol, progesterone, 25-OH vitamin D Total, aldosterone, cortisol, etc.), or molecular testing for infectious disease (ID), even though laboratories prefer the cost savings and automation offered by the large immunoassay analyzers.

Therefore, there is a clinical need for simple, inexpensive, automatable and effective microparticulate binding surface sample pretreatment solutions to deplete sample interference prior to the diagnostic test without impacting laboratory workflow and turnaround time. The same sample depletion approach can be used to develop new microparticulate binding surface sample enrichment solutions to support the LC-MS/MS Diagnostics Market for simple, inexpensive, and automatable serum enrichment or immunoaffinity of target biomarkers, and Molecular Diagnostics Market for sample preanalytical processing and nucleic acid purification and concentration for accurate, reproducible, clinically relevant molecular diagnostics for precision medicine.

DETAILED DESCRIPTION

The global immunoassay instruments and reagents market is expected to reach $19.1 billion by 2018, and in the U.S. alone up to 10 billion laboratory tests are performed each year (2-3). While MFG develop, optimize and validate their immunoassays to mitigate known mechanisms of heterophilic interference, assays can only manage interference if it is within their ABT (FIG. 4). There remain patient specimens in the clinical population with titers, avidity and mechanisms of heterophilic interference outside their ABT that may result in erroneous results that can impact patient care and lead to unnecessary invasive, diagnostic or therapeutic procedures (16-17, 28, 37-38, 48-49, 51).

While studies have demonstrated a prevalence of heterophilic interference from as low as 0.05% to as high as 80%, heterophilic antibodies (HAAA), rheumatoid factor (RF), and Manufacture assay specific interference (MASI) are the most troublesome and problematic mechanisms of interference as they are difficult to detect and can drastically affect patient management (4, 6, 14, 19, 21, 32, 34, 44, 45).

Human anti-animal antibody (HAAA) interference is primarily attributed to human heterophilic antibodies specific to bovine, goat, mouse, rabbit, or sheep IgG commonly used in immunoassays. Rheumatoid factor (RF) interference is specific to mouse IgG and Fc portion of antibodies used in immunoassays, and Manufacture assay specific interference (MASI) is primarily attributed to patient specific interference directly or indirectly (i.e. antibodies against) from diet, nutritional supplements, medications or medical therapy/treatment that bind or interact with immunoassay critical raw materials. Examples of MASI from some of the top 10 IVD companies include Abbott Laboratories (acridinium ester and streptavidin), Beckman Coulter (alkaline phosphatase and streptavidin), DiaSorin (ABEI and streptavidin), Ortho Clinical Diagnostics (horse radish peroxide), Roche Diagnostics (biotin, ruthenium and streptavidin), and Siemens Healthcare (fluorescein, acridinium ester, and anti-fluorescein antibody).

As the prevalence of interference can vary within a population, and between populations, so can the avidity and titer (concentration) of such heterophiles that makes it very difficult for Manufacturers to design around or 100% mitigate sample interference. While they add blockers, or optimize sample volume, incubation and wash parameters, they can only mitigate interference to a certain extent and would benefit from sample pre-treatment. Therefore, it is very difficult to impossible for Laboratories to differentiate specimens that have heterophilic interference resulting in falsely elevated or suppressed results in a given assay, from those specimens who do not have interference and result in correct and clinically accurate results. It is only those samples with atypically high or low results (or out of range results) that are currently detected by laboratories, while the majority of interference goes undetected. In fact, since most laboratories work with de-identified patient IDs, and do not have or review patient records, they would not know if they are reporting erroneous results unless the physician complains or notifies the lab that a given patient results) does not fit the clinical picture.

There is a clinical need for a simple, inexpensive, automatable and effective sample pre-treatment solution to mitigate HAAA, MASI and RF mechanisms of interference without impacting laboratory work flow and turnaround time, and without altering or changing the sample composition to enable laboratories to report patient results to physicians after such pre-treatment. Since immunoassays are developed, optimized and validated to mitigate known interference mechanisms based on the ABT, a sample pre-treatment solution does not need to completely deplete, remove or eliminate interference from the sample. As long as the interference titer, avidity and/or mechanism(s) falls within the ABT after sample pre-treatment, the assay design will successfully mitigate the residual sample interference and report an accurate patient result. Therefore, depletion in the context of this proposal does not necessarily imply 100% removal of interference from the sample but means that residual interference no longer results in an erroneous result. However, sample pre-treatment depletion can result in 100% removal of interference or target analyte(s) if required for a particular assay or purpose such as subsequent elution and analysis by LC-MS/MS, or for sample preanalytical processing, nucleic acid purification and concentration for molecular diagnostics, or for the enrichment of biomarkers from challenging sample types such as urine, saliva and stool.

Microparticulate surfaces can be coated with antibodies, proteins, enzymes, analytes or nucleic acids to pre-treat samples prior to analysis and without changing the composition or definition of the samples. Surfaces can be co-coated with animal antibodies or animal serum to block HAAA and RF interference, or co-coated with Manufacturer assay specific reagents such as streptavidin, ALP, HRP, BSA-fluorescein, BSA-ABEI, BSA-acridinium, or BSA-ruthenium to block MASI. Since interference can include small molecules, analogues of such small molecules can be conjugated to carrier proteins such as BSA using a variety of different linker strategies and linker lengths based on the MFG immunoassay conjugate and steric accessibility by the interfering antibodies or interfering proteins. For example, the ABEI used in DiaSorin assays could be conjugate to BSA for subsequent binding of BSA-ABEI to the microparticulate surface. The same would be true for fluorescein (Siemens), ruthenium and biotin (Roche), and acridinium ester (Abbott and Siemens). Larger proteins can be directly coupled to the microparticulate surface such as alkaline phosphatase (Beckman), streptavidin (Roche), and monoclonal anti-fluorescein antibody (Siemens).

While the examples describe and teach how microparticulate surface products could be used to deplete interference to fall within the ABT, these same products and approaches could also be used to target specific analytes for subsequent depleted-sample analysis by LC-MS/MS, molecular diagnostics, and/or immunoassays. For example, a sample could be pre-treated with a microparticulate binding surface product to deplete sex hormone-binding globulin (SHBG) or sex steroid-binding globulin (SSBG) from serum or plasma such that the SHBG-depleted sample could be subsequently tested to measure free or bioavailable hormone or steroid (i.e. free testosterone). As another example, the product could be used to isolate and purify a specific target in the sample for subsequent elution and testing, or to enrich the biomarker prior to the diagnostic test.

Example 1

Primary blood collection tubes (PBCT) are an ideal target for sample pre-treatment since such an approach would pre-treat samples and deplete interference as the blood is collected into the PBCT, and prior to the sample being tested by the laboratory. This approach would not impact laboratory WF or TAT, and depending on the cost of the custom PBCT, as well as who pays for the PBCT (payer, MFG, hospital, clinic, or laboratory), this approach may or may not add cost to the laboratory. Other advantages of this approach are that samples would have sufficient time to pre-incubate and bind to the blocking reagents prior to testing such that binding kinetics and time would not be major components of variance. It would also not dilute the sample, and if the microparticulate blocking reagent(s) and bound interference are completely sequestered to the tube surface prior to sample aspiration, the sample composition or definition would not change and the laboratory could report such results. Risks of the PBCT approach are that the blocking reagents may impact the performance or intended use/claims of the PBCT, may introduce a new source of interference or instability, could affect clotting or coagulation, or may not have sufficient surface area and binding capacity to sufficiently deplete the interference so that it falls within the ABT. In addition, sample size (volume of blood collected) and tube storage conditions may be highly variable and susceptible to human error.

Microparticulate binding surfaces coated with blocking reagents can be used to develop custom microparticles to pre-treat samples and deplete interference. Key advantages of this approach include, a) the microparticles have a very high surface area and binding capacity per unit mass; b) since the microparticles are superparamagnetic and move and coordinate very quickly in the presence of a magnetic field, a strong rare earth magnet (e.g. neodymium magnet) can be used to easily and quickly separate, sequester or remove particles from the sample; b) the microparticles can be lyophilized or dried down; and c) the microparticles can easily be blended or mixed with other microparticle types to make a custom microparticle formulation or plurality of microparticles, each with different functionality or specificity.

One microparticulate binding surface approach to pre-treat samples and deplete interference is to add microparticles to a PBCT and dry down or lyophilize the microparticles inside the PBCT. When blood is collected into the PBCT and mixed, the lyophilized or dried down microparticles will be reconstituted and dispersed in the sample for subsequent binding and capture of interference. Once the custom PBCT arrives to the laboratory for testing, the laboratory can separate the microparticles from the serum or plasma using a strong magnet for subsequent aspiration and dispense of the sample into a SST. Alternatively, the custom PBCT could be placed in a specialized sample rack that contains a magnet to separate the microparticles from the sample prior to aspiration and dispense by the test analyser or instrument (FIG. 13).

Example 2

Secondary Transfer Tubes (STT) is another tube-based approach to pre-treat samples and deplete interference to fall within the ABT. While the STT approach may be similar to PBCT regarding cost, STT may impact laboratory WF and TOT without automation, and may create a storage and waster burden on the laboratory in order to store, use and discard SST. Key advantages of this approach include, a) samples would have sufficient time to pre-incubate and bind to the blocking reagents prior to testing such that binding kinetics and time would not be major component of variance; b) sample volume would be controlled via a defined aspiration and dispense volume; c) the sample would not be diluted; d) the sample composition or definition would not change, and the laboratory could report STT results since the blocking reagents would be tightly bound to the tube surface and not free in solution or considered a new component of the sample composition; and e) this approach is also automatable using existing sample handling platforms available today.

Another microparticulate binding surface approach would be to transfer the sample from the PBCT into a STT, and then to add microparticles to the STT to bind and deplete interference. Ideally the volume of microparticles added to the STT is small to minimize sample dilution, but since the sample volume and microparticle volume are known the subsequent test result can easily be corrected for this dilution factor (FIG. 14).

If the laboratory wants to physically remove the microparticles from the PBCT or STT prior to testing of the depleted sample, this can be done manually or can be automated using a magnet inside a disposable pipette tip. The pipette tip containing the magnet would be inserted inside the custom PBCT to bind and collect the magnetic microparticles on the tip surface. Once the microparticles are fully captured by the pipette tip magnet, the pipette tip would be removed from the sample and discarded with the microparticles resulting in an essentially magnetic microparticle-free interference depleted sample (FIG. 15).

Example 3

It is also possible to prepare a plurality of different microparticles that can be subsequently mixed at different ratios to enhance their blocking ability. For example, one microparticulate binding surface type may be coated with mouse IgG, polymerized mouse IgG, antibody fragments (Fc, Fab, F(ab')2) and different subclasses (IgG1, IgG2a, IgG2b, IgG3) of mouse IgG to target HAMA and RF interference mechanisms. A second microparticulate binding surface type may be coated with purified animal polyclonal antibodies (i.e. bovine, goat, mouse, rabbit, sheep) to target HAAA interference, and a third microparticle type could be coated with streptavidin, ALP, HRP, BSA (conjugated to isoluminol, ruthenium, acridinium) to target MASI interference (FIGS. 13-15). However, the disadvantages are cost since some microparticles are expensive, and sample contamination is possible if the magnetic beads are not completely removed from the samples or sequestered to the tube walls by the magnet. Any residual beads in the serum or plasma could alter the sample composition or definition, and may impact the accuracy of the test or present a new interference mechanism to the test.

The present invention is based at least in part on the realization that designing microparticulate binding surface for the depletion and enrichment of sample interferences or sample biomarkers, by: a) couple to the microparticulate binding surface, a binder, binding partner, capture moiety or combinations thereof; b) block the binding surface with a protein, polymer, surfactant, detergent, or combinations thereof to mitigate non-specific binding to the binding surface; c) contact and incubate of a plurality of microparticulate binding surfaces with the sample prior to the diagnostic test; d) bind known sample interferences and interference mechanisms, or biomarkers, by the microparticulate binding surface; e) the amount, mass, molarity, or concentration of interferences or interference mechanisms captured by the microparticulate binding surfaces results in a decreased or reduced amount, mass, molarity, or concentration of sample interferences that subsequently falls within the assay blocking threshold, or the assay formulation and design, to mitigate known sample interferences of the diagnostic test; f) for enrichment applications, the amount, mass, molarity, concentration, or yield of targeted biomarkers captured by the microparticulate binding surfaces is sufficient for subsequent analysis and qualitative, semi-quantitative or quantitative diagnostic testing; and g) separate, remove or eliminate the microparticulate binding surface from the sample, can result in more desirable qualities for conducting diagnostic tests, such as affinity assays (e.g., immunoassays or nucleic acid assays), than testing samples with known interferences or interference mechanisms.

The compositions and methods of the invention include improvements to assay performance parameters comprising accuracy, specificity, sensitivity (signal-to-noise ratio), assay precision (quantitative assays), and assay reproducibility (qualitative assays).

Known interference mechanisms can be, but not limited to, heterophile or heterophile-like interferences such autoantibodies, rheumatoid factor (RF), human anti-mouse antibodies (HAMA), human anti-animal antibodies (HAAA) such as goat, rabbit, sheep, bovine, mouse, horse, pig, and donkey polyclonal and/or monoclonal antibodies, and Manufacture assay-specific interference used in the test design or assay formulation such as the chemiluminescent substrate (isoluminol, ABEI, ruthenium, acridenium ester), fluorescent label (fluorescein or other fluorophores and dyes), capture moieties (streptavidin, neutravidin, avidin, polyA, polyDT, aptamers, antibodies, Fab, F(ab')2, antibody fragments, recombinant proteins, enzymes, proteins, biomolecules, polymers) and their binding partners (i.e. biotin, fluorescein, PolyDT, PolyA, antigen, etc.), conjugation linkers (LC, LC-LC, PEO, $PEO_n$), and solid phase blocking proteins (bovine serum albumin, human serum albumin, ovalbumin, gelatin, purified poly- and monoclonal IgG such as mouse, goat, sheep and rabbit, polyvinyl alcohol or PAA, polyvinylpyrrolidone or PVP, Tween-20, Tween-80, Triton X-100, triblock copolymers such as Pluronic and Tetronic, and other commercially available blockers, blocking proteins and polymer-based blocking reagents such those from Surmodics and Scantibodies) typically used in the design of antibody-based diagnostic tests, non-antibody based diagnostic testes, or sample pre-treatment methods and devices for subsequent analysis by mass spectrometry (i.e. HPLC, MS, LCMS, LC-MS/MS), radioimmunoassay (RIA), enzyme-linked immunoassay (ELISA), chemiluminescence immunoassay (CLIA), molecular diagnostics, lateral flow, point-of-care (PoC), CLIA and CLIA waived tests and devices.

A Diagnostic Test comprises any antibody-based diagnostic test, non-antibody based diagnostic test, a sample pre-treatment method or device for subsequent analysis by chromatographic, spectrophotometric, and mass spectrometry methods (i.e. HPLC, MS, LCMS, LC-MS/MS) such as immunoextraction (IE) and solid phase extraction (SPE), radioimmunoassay (RIA), enzyme-linked immunoassay (ELISA), chemiluminescence immunoassay (CLIA), molecular diagnostics, lateral flow (LF), point-of-care (PoC), direct to consumer (DTC), CLIA and CLIA waived tests and devices, Research Use Only (RUO) test, In Vitro Diagnostics (IVD) test, Laboratory Developed Test (LDT), companion diagnostic, and any test for diagnosis, prognosis, screening, risk assessment, risk stratification, and monitoring such as therapeutic drug monitoring.

Affinity assays include assays that determine the presence or absence of an analyte in a sample, and/or quantitate the amount of analyte in a sample, directly or indirectly, based on a specific or relatively specific interaction between the analyte and a molecule that preferentially binds the analyte. Affinity assays include assays that rely in at least some respect on a specific or relatively specific binding affinity of one entity for another. Affinity assays include, but are not limited to, assays that rely on a binding interaction between a receptor and a ligand, an enzyme and its substrate, a polynucleotide and its complement or substantial complement, a small molecule and a binding protein that binds the small molecule with specificity, etc. Immunoassays include assays that rely on the interaction between, for example, an antigen and an antibody that recognizes the antigen. Immunoassays also include, for example, assays that employ an antibody or fragment thereof to bind an antigen of interest in a sample. Affinity assays also include, for example, competitive assays and sandwich assays. Such assays include those which rely on an interaction of a surface-bound antigen to detect an antibody of interest in a sample, and those that interaction of a surface-bound antibody or fragment thereof to detect an antigen of interest in a sample. As used herein, antigens are not limited to polypeptides or proteins, but can also include small molecules (such as, for example, haptens) and antibodies (for example, antibodies can be used as antigens to generate other antibodies that recognize them). In general, antigen as used herein includes any analyte of interest in a sample immunoassayed with an antibody or fragment thereof using the compositions or methods of the invention.

The Assay Blocking Threshold (ABT) comprises the diagnostic test design or assay formulation to mitigate known mechanisms of sample interference regardless of the titer (concentration), avidity (attraction or affinity to the assay reagents), and mechanism(s) such as: a) specific type of blocker(s) used in the assay; b) concentration or quantity of blocker(s) used in the assay; c) which assay reagents (solid phase, conjugate/tracer, assay buffers, pre-treatment buffer, etc.) have blocker(s) in their respective diluents; d) how long the blockers incubate with the sample; e) the sample volume; f) the assay reagent volumes and sample dilution factor during the assay; g) the assay steps; h) the number of washes, i) the sequence of washes (i.e. 1-step, 2-step, etc.); j) the use of an assay buffer(s) to dilute the sample; k) the use of an assay buffer to store blockers and pre-treat the sample, and l) order of addition (i.e. sample pre-treatment, delayed addition/Piggy Back, etc.).

A Sample is defined as, but not limited to, any human or animal serum, plasma (i.e. EDTA, lithium heparin, sodium citrate), blood, whole blood, processed blood, urine, saliva, stool (liquid and solid), semen or seminal fluid, cells, tissues, biopsy material, DNA, RNA, or any fluid, dissolved solid, or processed solid material to be tested for diagnosis, prognosis, screening, risk assessment, risk stratification, and monitoring such as therapeutic drug monitoring.

Samples can be collected into in a primary blood collection tube (PBCT), secondary transfer tube (SST), 24-hour (24-hr) urine collection device, a saliva collection tube, blood spot filter paper, or any collection tube or device such as for stool and seminal fluid, a light green top or green top plasma separator tube (PST) containing sodium heparin, lithium heparin or ammonium heparin, a light blue top tube containing sodium citrate (i.e. 3.2% or 3.8%) or citrate, theophylline, adenosine, dipyridamole (CTAD), a red top tube for Serology or Immunohematology for the collection of serum in a glass (no additives) or plastic tube (contains clot activators), a red top tube for Chemistry for the collection of serum in a glass (no additives) or plastic tube (contains clot activators), a purple lavender top tube containing EDTA K2, EDTA K3, liquid EDTA solution (i.e. 8%), or EDTA K2/gel tubes for testing plasma in molecular diagnostics and viral load detection, a pink top tube for Blood Bank EDTA, a gray top tube containing potassium oxalate and sodium fluoride, sodium fluoride/EDTA, or sodium fluoride (no anticoagulant, will result in a serum sample), a yellow top tube containing ACD solution A or ACD solution B, a royal blue top (serum, no additive or sodium heparin), a white top tube, or any color or tube type, for any application or diagnostic test type, containing no additives or any additive or combinations thereof, for the collection of blood.

A primary blood collection tube (PBCT) and secondary transfer tube (SST) can be any commercially available standard or custom collection tube (with or without gel separators) from companies like Becton Dickinson (BD), Greiner, VWR, and Sigma Aldrich, a glass tube, a plastic tube, a light green top or green top plasma separator tube (PST) containing sodium heparin, lithium heparin or ammonium heparin, light blue top tube containing sodium citrate (i.e. 3.2% or 3.8%) or citrate, theophylline, adenosine, dipyridamole (CTAD), red top tube for Serology or Immunohematology for the collection of serum in a glass (no additives) or plastic tube (contains clot activators), a red top tube for Chemistry for the collection of serum in a glass (no additives) or plastic tube (contains clot activators), a purple lavender top tube containing EDTA K2, EDTA K3, liquid EDTA solution (i.e. 8%), or EDTA K2/gel tubes for testing plasma in molecular diagnostics and viral load detection, a pink top tube for Blood Bank EDTA, a gray top tube containing potassium oxalate and sodium fluoride, sodium fluoride/EDTA, or sodium fluoride (no anticoagulant, will result in a serum sample), a yellow top tube containing ACD solution A or ACD solution B, a royal blue top (serum, no additive or sodium heparin), a white top tube, or any color or tube type, for any application or diagnostic test type, containing no additives or any additive or combinations thereof, for the collection of blood.

The sample for biomarker enrichment can be any human or animal serum, plasma (i.e. EDTA, lithium heparin, sodium citrate), blood, whole blood, processed blood, urine, saliva, stool (liquid and solid), semen or seminal fluid, cells, tissues, biopsy material, DNA, RNA, or any fluid, dissolved solid, or processed solid material, but preferably is a challenging sample type such as urine, 24-hour urine, saliva and stool where the biomarker may be dilute or difficult to measure without microparticulate binding surface enrichment and concentration prior to the diagnostic test, or for methods that require sample pre-treatment or immunoaffinity capture prior to the diagnostic test such as HPLC, MS, LC-MS/MS, and molecular diagnostics.

In various embodiments, the microparticulate binding surface comprises an organic polymer or copolymer. In various embodiments, the organic polymer or copolymer is hydrophobic. Suitable polymers include, but are not limited to, polystyrene, poly(divinylbenzene), styrene-acylate copolymer, styrene-butadiene copolymer, styrene-divinylbenzene copolymer, poly(styrene-oxyethylene), polymethyl methacrylate, polyurethane, polyglutaraldehyde, polyethylene imine, polyvinylpyrrolidone, N,N'-methylene bis-acrylamide, polyolefeins, polyethylene, polypropylene, polyvinylchloride, polyacrylonitrile, polysulfone, poly(ether sulfone), pyrolized materials, block copolymers, and copolymers of the foregoing, silicones, or silica.

As used herein, coupled with, or its grammatical equivalents, means a covalent or non-covalent binding or interaction between two moieties. The term coupled with is not intended to connote an orientation Or direction of the coupling (1).

The term "coupled" includes (a) covalent binding (e.g., through one or more carbon-carbon bonds, carbon-nitrogen bonds, carbon-oxygen bonds, etc., either directly or indirectly), and (b) non-covalent binding (either indirectly or directly).

Entities that are known to specifically interact with one another can be covalently coupled. One non-limiting example of entities that are known to specifically interact and that can be covalently coupled is an antigen and its specific antibody, which can be made to covalently attach through, for example, coupling chemistry.

Entities that do not specifically interact with one another can be covalently coupled. One non-limiting example of entities that are not known to specifically interact with one another and that can be covalently coupled is SA and BSA, which can be made to covalently attach through, for example, coupling chemistry.

Examples of non-covalent binding include, affinity, ionic, van der Waals (e.g., dipole/dipole or London forces), hydrogen bonding (e.g., between polynucleotide duplexes), and hydrophobic interactions. Where association is non-covalent, the association between the entities is preferably specific. Non-limiting examples of specific non-covalent associations include the binding interaction between biotin and a biotin-binding protein such as avidin, SA, neutravidin, a fragment of SA, a fragment of avidin, a fragment of neutravidin, or mixtures thereof; the binding of a biotinylated Fab, a biotinylated immunoglobulin or fragment thereof, a biotinylated small molecule (such as, for example, a hormone or a ligand of a receptor), a biotinylated polynucleotide, a biotinylated macromolecule (e.g., a protein or a natural or synthetic polymer) to a biotin-binding protein such as avidin, SA, neutravidin, a fragment of SA, a fragment of avidin, a fragment of neutravidin, or mixtures thereof; the binding of a substrate to its enzyme; the binding of a glycoprotein to a lectin specific for the glycoprotein; the binding of a ligand to a receptor specific for the ligand; the binding of an antibody to an antigen against which the antibody is raised; and duplex formation between a polynucleotide and a complementary or substantially complementary polynucleotide; etc.

Most commercially available microparticles are polystyrene-based, and protein absorption to the microparticle surface occurs passively (e.g., by hydrophobic and/or ionic interaction) and nonspecifically. Although a tosyl-activated microparticle is shown, the support can be activated with any suitable functional group (e.g., carboxylic acid, epoxy, etc.) that can covalently bind the binder, binding partner, capture moiety functional groups (e.g., the primary amino or sulfhydryl groups).

In various embodiments of the present invention, the binder, binding partner or capture moiety can be covalently bound to the microparticulate binding surface or non-covalently bound to the microparticulate binding surface. In a specific embodiment, the binder, binding partner or capture moiety is covalently bound to the microparticulate binding surface.

In other embodiments, covalently coupling of the binder, binding partner or capture moiety to the microparticulate binding surface is optional. For example, where the binder, binding partner or capture moiety is hydrophobic, the binder, binding partner or capture moiety can be non-covalently coupled with the microparticulate binding surface.

The microparticulate binding surface can comprise an organic polymer or copolymer such as a material selected from the group consisting of, but not limited to, ceramic, glass, a polymer, a copolymer, a metal, latex, silica, a colloidal metal such as gold, silver, or alloy, polystyrene, derivatized polystyrene, poly(divinylbenzene), styrene-acylate copolymer, styrene-butadiene copolymer, styrene-divinylbenzene copolymer, poly(styrene-oxyethylene), polymethyl methacrylate, polymethacrylate, polyurethane, polyglutaraldehyde, polyethylene imine, polyvinylpyrrolidone, polyvinyl alcohol, polyacrylic acid, N,N'-methylene bis-acrylamide, polyolefeins, polyethylene, polypropylene, polyvinylchloride, polyacrylonitrile, polysulfone, poly(ether sulfone), pyrolized materials, block copolymers, and copolymers of the foregoing, silicones, or silica, methylol melamine, a biodegradable polymer such as dextran or poly (ethylene glycol)-dextran (PEG-DEX), or combinations thereof.

In various embodiments the support comprises a microparticle. In a specific embodiment, the microparticle comprises a paramagnetic or superparamagnetic material such as, for example, ferromagnetic iron oxide $Fe_3O_4$ or $Fe_2O_3$, or maghemite. The terms "paramagnetic" and "superparamagnetic" refer to materials that experience a force in a magnetic field gradient, but do not become permanently magnetized.

In various embodiments, the mean diameter of the microparticle is in the range of 40 nm to 3000 nm. In a specific embodiment, the mean diameter of the microparticle is in the range of about 100 nm to about 1,100 nm. In another specific embodiment, the mean diameter of the microparticle is in the range of about 100 nm to about 500 nm.

The microparticle support surface comprises functional groups or a plurality of functional groups for covalent attachment (coupling, conjugation or binding) of a binder, binding partner, capture moiety or combinations thereof such as carboxyl, tosyl, epoxy, amine, sulfhydryl, hydroxyl, ester, and maleimide, click chemistry functionality [Copper (I)-Catalyzed Azide-Alkyne Cycloaddition (CuAAC), Strain-promoted Azide-Alkyne Cycloaddition (SPAAC), Strain-promoted Alkyne-Nitrone Cycloaddition (SPANC), and Reactions of Strained Alkenes such as Alkene and Azide [3+2] cycloaddition, Alkene and Tetrazine inverse-demand Diels-Alder, and Alkene and Tetrazole photoclick reaction], hydrazone-based coupling functionality such as S-HyNic (succinimidyl-6-hydrazino-nicotinamide) and S-4FB (N-succinimidyl-4-formylbenzamide) heterobifunctional crosslinkers, and photoreactive chemistries.

The microparticulate binding surface further comprising a binder or binding partner selected from the group consisting of an antibody, a fragment of an antibody, a polymer of antibody, a polymer of antibody fragments, a polymer of antibody and antibody fragments, a receptor, a ligand of a receptor, a ligand binder, a ligand of a ligand binder, an enzyme, an irreversibly inactivated enzyme, alkaline phosphatase, horse radish peroxidase, a peptide, a protein, a polymer, a fluorophore, a fluorescent dye, a quantum dot (Qdot), a fluorescent protein label, a DNA stain, a chemical, and a chemiluminescence chemical such as luminol, isoluminol, derivatives of isoluminol, acridinium ester, ruthenium and N-(4-aminobutyl)-N-ethyl-isoluminol (ABEI), amine-reactive labeling reagents such as, for example, sulfo-NHS-biotin, sulfo-NHS-LC-biotin, sulfo-NHS-LC-LC-biotin, sulfo-NHS-SS-biotin, NHS-PEO$_4$-biotin, NHS-biotin, NHS-LC-biotin, NHS-LC-LC-biotin, PFP-biotin, TFP-PEO-biotin, or NHS-iminobiotin trifluoroacetamide, sulfhydryl-reactive biotin labeling reagents such as, for example, maleimide-PEO$_2$-biotin, biotin-BMCC, PEO-Iodoacetyl biotin, iodoacetyl-LC-biotin, or biotin-HPDP, carboxyl-reactive biotin labeling reagents such as, for example, biotin PEO-amine or biotin PEO-LC-amine, carbohydrate-reactive biotin labeling reagents such as, for example, biocytin hydrazide, biotin hydrazide, or biotin-LC-hydrazide, and photoreactive biotin labeling reagents such as, for example, psoralen-PEO-biotin.

In various embodiments, the binders, binding partners and capture moieties are covalently coupled with the support. In embodiments where the binders, binding partners and capture moieties are covalently coupled with the support, any suitable binding chemistry known in the art can be used to attach the support coupler to the support. Suitable binding chemistries include, but are not limited to, attachment through one or more functional groups selected from the group consisting of carboxyl, hydroxyl, tosyl, epoxy, aldehyde, amine, amide, hydrazide, isothiocyanate, maleimide, and sulfhydryl.

Biomarkers comprise any analyte, antigen, small molecule, large molecule, drug, therapeutic agent, peptide, protein, protein digest, viral antigen, bacteria, cell, cell lysate, cell surface marker, epitope, antibody, a fragment of an antibody, IgG, IgM, IgA, receptor, a ligand of a receptor, hormone, a receptor of a hormone, enzyme, a substrate of an enzyme, a single stranded oligonucleotide, a single stranded polynucleotide, a double stranded oligonucleotide, a double stranded polynucleotide, polymer and aptamer.

A protein can be, for example, a monomer, a dimer, a multimer, or a fusion protein. In specific embodiments, the protein comprises at least one of an albumin such as, for example, antibody, a fragment of an antibody, BSA, ovalbumin, a fragment of BSA, a fragment of ovalbumin, mouse IgG, polymerized mouse IgG, antibody fragments (Fc, Fab, F(ab')2) and different subclasses (IgG1, IgG2a, IgG2b, IgG3) of mouse IgG to target HAMA and RF interference mechanisms, purified animal polyclonal antibodies (i.e. bovine, goat, mouse, rabbit, sheep) to target HAAA interference, streptavidin, ALP, HRP, BSA (conjugated to isoluminol, ruthenium, acridinium) to target MASI interference or mixtures thereof.

As used herein, the term "fusion protein" encompasses recombinant proteins (such as chimeric proteins), hybrid proteins, and synthetically-derived proteins. Its usage is well known in the art.

Suitable conjugation reagents for attaching biotin to an antibody or protein include amine-reactive labeling reagents such as, for example, sulfo-NHS-biotin, sulfo-NHS-LC-biotin, sulfo-NHS-LC-LC-biotin, sulfo-NHS-SS-biotin, NHS-PEO$_4$-biotin, NHS-biotin, NHS-LC-biotin, NHS-LC-LC-biotin, PFP-biotin, TFP-PEO-biotin, or NHS-iminobiotin trifluoroacetamide, sulfhydryl-reactive biotin labeling reagents such as, for example, maleimide-PEO$_2$-biotin, biotin-BMCC, PEO-Iodoacetyl biotin, iodoacetyl-LC-biotin, or biotin-HPDP, carboxyl-reactive biotin labeling reagents such as, for example, biotin PEO-amine or biotin PEO-LC-amine, carbohydrate-reactive biotin labeling reagents such as, for example, biocytin hydrazide, biotin hydrazide, or biotin-LC-hydrazide, or photoreactive biotin labeling reagents such as, for example, psoralen-PEO-biotin. Similar chemistries and linkers can be used to conjugate assay signal detecting molecules such as ALP, HRP, luminol, isoluminol, isoluminol derivatives, ABEI, ABEI derivatives, acridinium ester, acridinium ester derivatives, fluorophores, fluorescein and enzymes to proteins and antibodies to prepare the conjugate used in an immunoassay (RIA, ELISA, CLIA, LF, PoC).

In a specific embodiment of the method for coating, the binder, binding partner or capture moiety is coupled with the support or the support coupler with an amine reactive reagent such as sulfo-NHS-LC-biotin.

In various embodiments, the method for coating further comprises at least one of an antibody, a binding fragment of an antibody, a receptor, a ligand of a receptor, a hormone, a receptor of a hormone, an enzyme, a substrate of an enzyme, a single stranded oligonucleotide, a double stranded oligonucleotide, a single stranded polynucleotide, a double stranded polynucleotide, an antigen, a peptide, or a protein.

In another aspect, a microparticulate binding surface comprising a capture moiety selected from the group consisting of an antibody, a binding fragment of an antibody, a IgG, a IgM, a IgA, a receptor, a ligand of a receptor, a hormone, a receptor of a hormone, an enzyme, a substrate of an enzyme, a single stranded oligonucleotide, a single stranded polynucleotide, a double stranded oligonucleotide, a double stranded polynucleotide, an antigen, a peptide, a polymer, an aptamer, and a protein.

Suitable capture moieties include at least one of an antibody, a binding fragment of an antibody, a receptor, a ligand of a receptor, a hormone, a receptor of a hormone, an enzyme, a substrate of an enzyme, a single stranded oligonucleotide, a double stranded oligonucleotide, a single polynucleotide, a double stranded polynucleotide, an antigen, a peptide, or a protein.

The microparticulate binding surface can further comprise a blocker selected from the group consisting of a protein such as albumin, bovine serum albumin, human serum albumin, ovalbumin, gelatin, casein, acid hydrolyzed casein, gama globulin, purified IgG, animal serum, polyclonal antibody, and monoclonal antibody, a polymer such as polyvinyl alcohol (PVA) and polyvinylpyrrolidone (PVP), a combination of a protein and polymer, a peptide, a PEGylation reagent such as (PEO) NHS or $(PEO)_n$-maleimide, a triblock copolymer such as Pluronic F108, F127, and F68, a non-ionic detergent such as Triton X-100, polysorbate 20 (Tween-20), and Tween 80 (non-ionic), a zwitterionic detergent such CHAPS, a ionic detergent such as sodium dodecyl sulfate (SDS), deoxycholate, cholate, and sarkosyl, a surfactant, a sugar such as sucrose, and a commercial blocker such as Heterophilic Blocking Reagent (Scantibodies), MAK33 (Roche Diagnostics), Immunoglobulin Inhibiting Reagent (IIR) (Bioreclamation), Heteroblock (Omega Biologicals), Blockmaster (JSR), TRU Block (Meridian Life Sciences), and StabilCoat® & StabilGuard® (Surmodics).

Microparticles can be added to a collection device such as a primary blood collection tube, 24-hr urine collection device, a urine collection device, a saliva collection tube, a stool collection device, a seminal fluid collection device, a blood collection bag, or any sample collection tube or device, prior to the addition of the sample.

Microparticles can also be added to a sample after collection of the sample into a collection tube or device, or after the transfer of the sample from a primary collection device into a storage or transfer device such as a plastic or glass tube, vial, bottle, beaker, flask, bag, can, microtiter plate, ELISA plate, 96-well plate, 384-well plate 1536 well plate, cuvette, reaction module, reservoir, or any container suitable to hold, store or process a liquid sample.

Microparticulate binding surface depletion of known interference mechanisms is defined as the complete or partial microparticle capture and binding to the microparticle surface target interference(s) or interference mechanisms such as heterophile or heterophile-like interferences, autoantibodies, rheumatoid factor (RF), human anti-mouse antibodies (HAMA), human anti-animal antibodies (HAAA) such as goat, rabbit, sheep, bovine, mouse, horse, pig, and donkey polyclonal and/or monoclonal antibodies, and Manufacture assay-specific interference used in the test design or assay formulation such as the chemiluminescent substrate (isoluminol, ABEI, ruthenium, acridenium ester), fluorescent label (fluorescein or other fluorophores and dyes), capture moieties (streptavidin, neutravidin, avidin, polyA, polyDT, aptamers, antibodies, Fab, F(ab')2, antibody fragments, recombinant proteins, enzymes, proteins, biomolecules, polymers) and their binding partners (i.e. biotin, fluorescein, PolyDT, PolyA, antigen, etc.), conjugation linkers (LC, LC-LC, PEO, $PEO_n$), and solid phase blocking proteins (bovine serum albumin, human serum albumin, ovalbumin, gelatin, purified poly- and monoclonal IgG such as mouse, goat, sheep and rabbit, polyvinyl alcohol or PAA, polyvinylpyrrolidone or PVP, Tween-20, Triton X-100, triblock copolymers such as Pluronic and Tetronic, and other commercially available blockers and blocking proteins such those from Surmodics and Scantibodies) from human or animal serum, plasma (i.e. EDTA, lithium heparin, sodium citrate), blood, whole blood, processed blood, urine, saliva, stool (liquid and solid), semen or seminal fluid, cells, tissues, biopsy material, DNA, RNA, or any fluid or solid tested or analyzed by antibody-based diagnostic tests, non-antibody based diagnostic testes, or sample pre-treatment methods and devices for subsequent analysis by mass spectrometry (i.e. HPLC, MS, LCMS, LC-MS/MS), radioimmunoassay (RIA), enzyme-linked immunoassay (ELISA), chemiluminescence immunoassay (CLIA), molecular diagnostics, lateral flow, point-of-care, CLIA and CLIA waived tests and devices. Depletion is defined as complete if sufficient quantity of interference(s) or interference mechanism(s) is captured for subsequent interference-free or reduced quantitative, semi-quantitative, or qualitative analysis, and is defined as partial if sufficient quantity of interference(s) or interference mechanism(s) is captured for subsequent semi-quantitative or qualitative analysis, or also partial if sufficient quantity of interference(s) or interference mechanism(s) and internal standard(s) is captured for quantitative, semi-quantitative or qualitative analysis by measurement methods that can use internal standards to adjust for recovery of the target analyte(s) such as LCMS and LC-MS/MS (i.e. deuterated internal standard) and HPLC (C14 or tritiated internal radioisotope internal standards). Successful depletion of the interference(s) or interference mechanism(s) can also be defined as the quantity of interference(s) or interference mechanism(s) that needs to be removed or depleted from the sample type prior to analysis, testing or measurement that falls within the assay blocking threshold (ABT) of the diagnostic test such that the test design will successful block or mitigate any residual interference(s) or interference mechanism(s) after microparticle-based depletion and report an accurate or high quality result.

A method to make a multi-functional microparticulate binding surface for the depletion of more than one sample interference comprising: a) pool 2 or more microparticulate binding surfaces that contain different binders, binding partners or capture moieties to make a plurality of microparticulate binding surfaces to target more than 1 interference or interference mechanism in the same sample; b) add the microparticulate binding surface pool to the sample; b) mix the sample with microparticulate binding surfaces; c) incubate microparticulate binding surfaces with the sample to bind the targeted interferences; d) separate, remove or eliminate the microparticulate binding surfaces from the sample; e) test the essentially microparticulate binding surface-free sample by the diagnostic test.

A method of depleting sample interferences from a sample prior to the diagnostic test consisting: a) add a microparticulate binding surface to the sample; b) mix the sample with microparticulate binding surface; c) incubate the microparticulate binding surface with the sample to bind and capture the targeted interferences and interference mechanisms to the microparticulate binding surface; d) separate, remove or eliminate the microparticulate binding surface from the sample to prepare an essentially microparticulate binding surface-free sample supernatant; e) test the essentially microparticulate binding surface-free sample by the diagnostic test.

A method to deplete sample interference where: a) the microparticulate binding surface (microparticles) is lyophilized; b) the lyophilized microparticles are a pellet or sphere such as a LyoSphere™ (BIOLYPH LLC); c) the lyophilized microparticles are Manufactured into custom primary blood collection tubes (PBCT); d) the final PBCT contains a lyophilized pellet or pellets of the microparticles and are protected from moisture and humidity to preserve the stability of the lyophilized pellets so they remain lyophilized until contact with the sample; e) when the sample is collected into the PBCT the lyophilized microparticles are reconstituted (solubilized) and mixed into the sample; f) the microparticles bind the targeted interferences in the PBCT; g) separate, remove or eliminate the microparticulate binding surfaces from the sample; h) essentially microparticulate binding surface-free sample by the diagnostic test.

A method to deplete sample interference where the PBCT is used for short turn-around time (STAT) diagnostic tests, ambulatory tests, lateral flow tests, point of care (PoC) tests, molecular diagnostic tests, HPLC, MS, LCMS, LC-MS/MS, radioimmunoassay (RIA), enzyme-linked immunoassay (ELISA), chemiluminescence immunoassay (CLIA), CLIA and CLIA waived tests, and any diagnostic test used for the diagnosis, prognosis, screening, risk assessment, risk stratification, treatment monitoring, and therapeutic drug monitoring.

An essentially microparticulate binding surface-free is where there is 0.00% (w/v) to <1.00% (w/v) microparticulate binding surface remaining, or preferably 0.00% (w/v) to <0.10% (w/v) microparticulate binding surface remaining, or more preferably 0.00% (w/v) to <0.01% (w/v) microparticulate binding surface remaining.

A method to separate, remove or eliminate the microparticulate binding surface from the sample consisting of: a) centrifugation at 1000×g or greater for long enough (in some embodiments for at least 5 minutes to spin-down the microparticles and to form a pellet of microparticles at the bottom of the centrifuge tube (container) and to form an essentially microparticle-free sample supernatant; b) carefully aspirate (remove) the essentially microparticle-free supernatant without disrupting the microparticle pellet or without removing any microparticles; c) test the essentially microparticle-free sample by the diagnostic test.

A method to separate, remove or eliminate the microparticulate binding surface from the sample consisting of: a) select a fitter material with a porosity or molecular weight cut-off (MWCO) sufficiently smaller than the diameter of the microparticulate binding surface such that the microparticles will not pass through the fitter; b) add the sample with microparticulate binding surface to the filtration device and filter; c) gravity-, vacuum- or centrifuge-filter the sample into the collection device such that the filtrate is essentially microparticulate binding surface-free; c) test the essentially microparticulate binding surface-free sample by the diagnostic test.

A method to separate, remove or eliminate the microparticulate binding surface from the sample consisting of: a) using a strong magnet such as a neodymium magnet to completely separate the magnetic, paramagnetic or superparamagnetic microparticulate binding surface and to form a pellet of microparticles on the sides or bottom of the sample container and to form an essentially microparticulate binding surface-free sample supernatant; b) carefully aspirate (remove) the essentially microparticulate binding surface-free supernatant without disrupting the microparticle pellet or without removing any microparticles; c) test the essentially microparticulate binding surface-free sample by the diagnostic test.

A method to separate, remove or eliminate the microparticulate binding surface from the sample consisting of: a) insert the magnet into a disposable pipette tip, cover or sheath; b) insert the disposable pipette tip, cover or sheath with magnet into the sample to collect the magnetic, paramagnetic or superparamagnetic microparticulate binding surface on the surface of the pipette tip, cover or sheath such that the sample supernatant is essentially microparticulate binding surface-free; c) carefully aspirate (remove) the essentially microparticulate binding surface-free supernatant without disrupting the microparticle pellet or without removing any microparticles; d) test the essentially microparticulate binding surface-free sample by the diagnostic test.

Microparticle-based enrichment is defined as the complete or partial microparticle capture and binding of target analyte(s) to the microparticles surface from the human or animal serum, plasma (i.e. EDTA, lithium heparin, sodium citrate), blood, whole blood, processed blood, urine, saliva, stool (liquid and solid), semen or seminal fluid, cells, tissues, biopsy material, DNA, RNA, or any fluid or solid tested or analyzed by antibody-based diagnostic tests, non-antibody based diagnostic testes, or sample pre-treatment methods and devices for subsequent analysis by mass spectrometry (i.e. HPLC, MS, LCMS, LC-MS/MS), radioimmunoassay (RIA), enzyme-linked immunoassay (ELISA), chemiluminescence immunoassay (CLIA), molecular diagnostics, lateral flow, point-of-care, CLIA and CLIA waived tests and devices. Enrichment is defined as complete if sufficient quantity of anayte(s) is captured for subsequent quantitative, semi-quantitative, or qualitative analysis, and is defined as partial if sufficient quantity of analyte(s) is captured for subsequent semi-quantitative or qualitative analysis, or also partial if sufficient quantity of target analyte(s) and internal standard(s) is captured for quantitative, semi-quantitative or qualitative analysis by measurement methods that can use internal standards to adjust for recovery of the target analyte(s) such as LCMS and LC-MS/MS (i.e. deuterated internal standard) and HPLC (C14 or tritiated internal radioisotope internal standards). Enrichment of target analytes for subsequent automated, semi-automated, manual, CLIA, CLIA waived, Lateral Flow, or PoC analysis can be from any sample type tested by the laboratory, hospital, University, research laboratory, reference laboratory, center of excellence, laboratory developed test (LDT), Research Use Only (RUO), In Vitro Diagnostic (IVD) test, regulatory approved test (CE Marked, FDA 510(k), FDA PMA, FDA Class I(1), II(2) or III(3)), send-out testing site, primary care physicians (PCP) office, pharmacy, clinic, urgent care, point-of-care, consumer-based (home, pharmacy, drug store, grocery store or market, outside the doctor's office) such as human or animal serum, plasma (i.e. EDTA, lithium heparin, sodium citrate), blood, whole blood, processed blood, urine, saliva, stool (liquid and solid), semen or seminal fluid, cells, tissues, biopsy material, DNA, RNA, or any fluid or solid tested or analyzed by antibody-based diagnostic tests, non-antibody based diagnostic testes, or sample pre-treatment methods and devices for subsequent analysis by mass spectrometry (i.e. HPLC, MS, LCMS, LC-MS/MS), radioimmunoassay (RIA), enzyme-linked immunoassay (ELISA), chemiluminescence immunoassay (CLIA), molecular diagnostics, lateral flow, point-of-care, CLIA and CLIA waived tests and devices.

A method is presented for enriching a biomarker in a sample prior to the diagnostic test consisting: a) add a microparticulate binding surface to the sample; b) mix the sample with microparticulate binding surface; c) incubate the microparticulate binding surface with the sample to bind and capture the targeted biomarker to the microparticulate binding surface; d) separate or remove the microparticulate binding surface from the sample; e) save the microparticulate binding surface and discard the essentially microparticulate binding surface-free sample supernatant; f) wash the microparticulate binding surface using an appropriate wash diluent to remove non-specific materials; g) measure the amount, mass, molarity, concentration, or yield of targeted biomarker captured by the microparticulate binding surface using a qualitative, semi-quantitative or quantitative diagnostic test specific for the biomarker.

A method of measuring the amount, mass, molarity, concentration, or yield of targeted biomarker captured and enriched by the microparticulate binding surface whereby the biomarker is eluted, disassociated or freed from the microparticulate binding surface by disrupting the binding interaction using elution strategies such as pH (e.g. increased pH with a base such as sodium bicarbonate, decreased pH with an acids such as acetic acid, trichloroacetic acid, sulfosalicylic acid, HCl, formic acid, and common pH elution buffers such as 100 mM glycine.HCl, pH 2.5-3.0, 100 mM citric acid, pH 3.0, 50-100 mM triethylamine or triethanolamine, pH 11.5, 150 mM ammonium hydroxide, pH 10.5), a displacer or displacing agent, competitive elution (e.g. >0.1M counter ligand or analog), ionic strength and/or chaotropic effects (e.g. NaCl, KCl, 3.5-4.0M magnesium chloride pH 7.0 in 10 mM Tris, 5M lithium chloride in 10 mM phosphate buffer pH 7.2, 2.5M sodium iodide pH 7.5, 0.2-3.0M sodium thiocyanate), surfactant, detergent, a concentrated inorganic salt, denaturing (e.g. 2, 6M guanidine.HCl, 2-8M urea, 1% deoxycholate, 1% SDS), an organic solvent (e.g. alcohol, chloroform, ethanol, methanol, acetonitrile, hexane, DMSO, 10% dioxane, 50% ethylene glycol pH 8-11.5 (also chaotropic)), radiation or heat (increased temperature), conformational change, disulfide bond reducers (2-mercaptoethanol, dithiothreitol, tris(2-carboxylethyl)phosphine), enzyme inactivation, chaotropic agents (Urea, Guanidinium chloride, Lithium perchlorate), mechanical agitation, sonication, and protein digestive enzymes (pepsin, trypsin), and combinations thereof.

Unless otherwise stated, or implicit from the disclosure, any of the embodiments described in connection with any particular method or composition described herein can be used in conjunction with any of the other embodiments described herein.

The methods and compositions of the invention can be used in conjunction with any suitable assay known in the art, for example any suitable affinity assay or immunoassay known in the art including, but not limited to, protein-protein affinity assays, protein-ligand affinity assays, nucleic acid affinity assays, indirect fluorescent antibody assays (IFAS), enzyme-linked immunosorbant assays (ELISAs), radioimmunoassays (RIAs), and enzyme immunoassays (EIAs), direct or indirect assays, competitive assays, sandwich assays, etc. Suitable assay formats include, but are not limited to, assays and formats employed in the Examples herein.

The methods and compositions of the invention can be used in connection with any microparticulate binding surface, for example a suitable solid support, known in the art. Examples of such solid phase supports are discussed, but the invention is not limited to the supports explicitly discussed. For example, solid phase supports are not limited to particulate supports, to microparticles, to polystyrene microparticles, to microtiter plates, to coated tubes, etc. Other solid phase supports can also be used with the invention, including but not limited to any supports known in the art that are used in connection with affinity assays. For example, solid phase supports that comprise mylar-backed nitrocellulose, and/or nylon can be used. Solid phase supports that comprise filters or membranes, for example, can be used. Solid phase supports that comprise microtubules, nanoparticles, or nanotubes, for example, carbon nanotubes, can be used. Solid phase supports can comprise microparticles of any size and solid phase supports that have a large planar surface area can be used.

In at least one embodiment, the present invention provides a binding surface with two or more different capture moieties.

Itemized below is a nonlimiting list of substances that may function as one, or alternatively as the other, member of a binding pair consisting of analyte binder (capture moiety) and analyte, depending on the application for which an affinity assay is to be designed. Such substances can be used, for example, as capture moieties (analyte binders) or can be used to generate capture moieties (e.g., by employing them as haptens/antigens to generate specific antibodies) that can be used with the invention. Affinity assays, including immunoassays, can be designed in accordance with the invention to detect the presence and/or level of such substances where they are analytes in a sample. In a specific embodiment, the analyte-binding capture moieties of the invention can be used to detect these substances as analytes in a sample. Alternatively, the substances listed below can be associated with the solid phase support surface in accordance with the invention, and used to capture molecules that interact with them (such as, for example, antibodies or fragments thereof specific for the listed substances, binding proteins, or enzymes).

A nonlimiting list of substances that may function as one, or alternatively as the other, member of a binding pair consisting of analyte binder (capture moiety) and analyte includes: inducible nitric oxide synthase (iNOS), CA19-9, IL-1.alpha., IL-1.beta., IL-2, IL-3, IL-4, IL-t, IL-5, IL-7, IL-10, IL-12, IL-13, sIL-2R, sIL-4R, sIL-6R, SIV core antigen, IL-1RA, TNF-.alpha., IFN-gamma, GM-CSF; isoforms of PSA (prostate-specific antigen) such as PSA, pPSA, BPSA, in PSA, non-.alpha.sub.1-antichymotrypsin-complexed PSA, .alpha.sub.1-antichymotrypsin-complexed PSA, prostate kallikreins such as hK2, hK4, and hK15, ek-rhK2, Ala-rhK2, TVVT-rhK2, Xa-rhK2, HWT-rhK2, and other kallikreins; HIV-1 p24; ferritin, L ferritin, troponin I, BNP, leptin, digoxin, myoglobin, B-type natriuretic peptide or brain natriuretic peptide (BNP), NT-proBNP, CNP, NT-proCNP$_{(1-50)}$, NT-CNP-53$_{(51-81)}$, CNP-22$_{(82-103)}$, CNP-53$_{(51-103)}$, atrial natriuretic peptide (ANP); human growth hormone, bone alkaline phosphatase, human follicle stimulating hormone, human leutinizing hormone, prolactin; human chorionic gonadotrophin (e.g., CG.alpha., CG.beta.); soluble ST2, thyroglobulin; anti-thyroglobulin; IgE, IgG, IgG1, IgG2, IgG3, IgG4, B. anthracis protective antigen, B. anthrads lethal factor, B. anthracis spore antigen, F. tularensis LPS, S. aureas enterotoxln B, Y. pestis capsular F1 antigen, insulin, alpha fetoprotein (e.g., AFP 300), carcinoembryonic antigen (CEA), CA 15.3 antigen, CA 19.9 antigen, CA 125 antigen, HAV Ab, HAV Igm, HBc Ab, HBc Igm, HIV1/2, HBsAg, HBsAb, HCV Ab, anti-p53, histamine; neopterin; s-VCAM-1, serotonin, sFas, sFas ligand, sGM-CSFR, s1CAM-1, thymidine kinase, IgE, EPO, intrinsic factor Ab, haptoglobulin, anti-cardiolipin, anti-dsDNA, anti-Ro, Ro, anti-La, anti-SM, SM, anti-nRNP, antihistone, anti-Scl-70, Scl-70, anti-nuclear antibodies, anti-centromere antibodies, SS-A, SS-B, Sm, U1-RNP, Jo-1, CK, CK-MB, CRP, ischemia modified albumin, HDL, LDL, oxLDL, VLDL, troponin T, troponin I, troponin C, microalbumin, amylase, ALP, ALT, AST, GGT, IgA, IgG, prealbumin, anti-streptolysin, chlamydia, CMV IgG, toxo IgG, toxo IgM, apolipoprotein A, apolipoprotein B, C3, C4, properdin factor B, albumin, .alpha.sub.1-acid glycoprotein, .alpha.sub.1-antitrypsin, .alpha.sub.1-microglobulin, .alpha.sub.2-macroglobulin, anti-streptolysin O, antithrombin-III, apolipoprotein A1, apolipoprotein B, .beta.sub.2-microglobulin, ceruloplasmin, complement C3, complement C4, C-reactive protein, DNase B, ferritin, free kappa light chain, free lambda light chain, haptoglobin, immunoglobulin A, immunoglobulin A (CSF), immunoglobulin E, immunoglobulin G, immunoglobulin G (CSF), immunoglobulin G (urine), immunoglobulin G subclasses, immunoglobulin M, immunoglobulin M (CSF), kappa light chain, lambda light chain, lipoprotein (a), microalbumin, prealbumin, properdin factor B, rheumatoid factor, ferritin, transferrin, transferrin (urine), rubella IgG, thyroglobulin antibody, toxoplasma IgM, toxoplasma IgG, IGF-I, IGF-binding protein (IGFBP)-3, hepsin, pim-1 kinase, E-cadherein, EZH2, and a-methylacyl-CoA racemase, TGF-beta, IL6SR, GAD, IA-2, CD-64, neutrophils CD-64, CD-20, CD-33, CD-52, isoforms of cytochrome P450, s-VCAM-1, sFas, sICAM, hepatitis B surface antigen, thromboplastin, HIV p24, HIV gp41/120, HCV C22, HCV C33, hemoglobin A1c, and GAD65, IA.sub.2., vitamin D, 25-OH vitamin D, 1,25(OH)2 vitamin D, 24,25(OH)2 vitamin D, 25,26(OH)2 vitamin D, 3-epimer of vitamin D, FGF-23, sclerostin, procalcitonin, calcitonin, c. dificille toxin ABB, h. pylori, HSV-1, HSV2.

Suitable substances that may function as one, or alternatively as the other, member of a binding pair consisting of analyte binder (capture moiety) and analyte, depending on the application for which an affinity assay is to be designed, and that can be used with the present invention also include moieties, such as for example antibodies or fragments thereof, specific for any of the WHO International Biological Reference Preparations held and, characterized, and/or distributed by the WHO International Laboratories for Biological Standards (available at http:/www.who.int/blood-products/re_materials, updated as of Jun. 30, 2005, which lists substances that are well known in the art; the list is herein incorporated by reference).

A partial list of such suitable international reference standards, identified by WHO code in parentheses following the substance, includes: human recombinant thromboplastin (rTF/95), rabbit thromboplastin (RBT/90), thyroid-stimulating antibody (90/672), recombinant human tissue plasminogen activator (98/714), high molecular weight urokinase (87/594), prostate specific antigen (96/668), prostate specific antigen 90:10 (96/700); human plasma protein C (86/622), human plasma protein S (93/590), rheumatoid arthritis serum (W1066), serum amyloid A protein (92/680), streptokinase (00/464), human thrombin (01/580), bovine combined thromboplastin (OBT/79), anti-D positive control intravenous immunoglobulin (02/228), islet cell antibodies (97/550), lipoprotein a (IFCC SRM 2B), human parvovirus 619 DNA (99/800), human plasmin (97/536), human plasminogen-activator inhibitor 1 (92/654), platelet factor 4 (83/505), prekallikrein activator (82/530), human brain CJD control and human brain sporadic CJD preparation 1 and human brain sporadic CJD preparation 2 and human brain variant CJD (none; each cited in WHO TRS ECBS Report No. 926, 53.sup.rd Report, brain homogenate), human serum complement components C1q, C4, C5, factor B, and whole functional complement CH50 (W1032), human serum immunoglobulin E (75/502), human serum immunoglobulins G, A, and M (67/86), human serum proteins albumin, alpha-1-antitrypsin, alpha-2-macroglobulin, ceruloplasmin, complement C3, transferrin (W1031), anti-D negative control intravenous immunoglobulin (02/226), hepatitis A RNA (00/560), hepatitis B surface antigen subtype adw2 genotype A (03/262 and 00/588), hepatitis B viral DNA (97/746), hepatitis C viral RNA (96/798), HIV-1 p24 antigen (90/636), HIV-1 RNA (97/656), HIV-1 RNA genotypes (set of 10 I01/466), human fibrinogen concentrate (98/614), human plasma fibrinogen (98/612), raised A2 hemoglobin (89/666), raised F hemoglobin (85/616), hemoglobincyanide (98/708), low molecular weight heparin (85/600 and 90/686), unfractionated heparin (97/578), blood coagulation factor VIII and von Willebrand factor (02/150), human blood coagulation factor VIII concentrate (99/678), human blood coagulation factor XIII plasma (02/206), human blood coagulation factors II, VII, IX, X (99/826), human blood coagulation factors II and X concentrate (98/590), human carcinoembryonic antigen (73/601), human C-reactive protein (85/506), recombinant human ferritin (94/572), apolipoprotein B (SP3, 07), beta-2-microglobulin (B2M), human beta-thromboglobulin (83/501), human blood coagulation factor IX concentrate (96/854), human blood coagulation factor IXa concentrate (97/562), human blood coagulation factor V Leiden, human gDNA samples FV wild type, FVL homozygote, FVL heterozygote (03/254, 03/260, 03/248), human blood coagulation factor VII concentrate (97/592), human blood coagulation factor VIIa concentrate (89/688), human anti-syphilitic serum (HS), human anti-tetanus immunoglobulin (TE-3), human antithrombin concentrate (96/520), human plasma antithrombin (93/768), human anti-thyroglobulin serum (65/93), anti-toxoplasma serum (TOXM), human anti-toxoplasma serum (IgG) (01/600), human anti-varicella zoster immunoglobulin (W1044), apolipoprotein A-1 (SP1, 01), human anti-interferon beta serum (G038, 501, 572), human anti-measles serum (66/202), anti-nuclear ribonucleoprotein serum (W1063), anti-nuclear-factor (homogeneous) serum (66/233), anti-parvovirus B19 (IgG) serum (91/602), anti-poliovirus serum Types 1,2,3 (66/202), human anti-rabies immunoglobulin (RAI), human anti-rubella immunoglobulin (RUBI-1, 94), anti-smooth muscle serum (W1062), human anti-double-stranded DNA serum (Wo/80), human anti-E complete blood-typing serum (W1005), human anti-echinococcus serum (ECHS), human anti-hepatitis A immunoglobulin (97/646), human anti-hepatitis B immunoglobulin (W1042), human anti-hepatitis E serum (95/584), anti-human platelet antigen-1a (93/710), anti-human platelet antigen-5b (99/666), human anti-interferon alpha serum (B037, 501, 572), human alphafetoprotein (AFP), ancrod (74/581), human anti-A blood typing serum (W1001), human anti-B blood typing serum (W1002), human anti-C complete blood typing serum (W1004), anti-D (anti-RhO) complete blood-typing reagent (99/836), human anti-D (anti-RhO) incomplete blood-typing serum (W1006), and human anti-D immunoglobulin (1/572).

Other examples of suitable substances that may function as one, or alternatively as the other, member of a binding pair consisting of analyte binder (capture moiety) and analyte, depending on the application for which an affinity assay is to be designed include compounds that can be used as haptens to generate antibodies capable of recognizing the compounds, and include but are not limited to, any salts, esters, or ethers, of the following: hormones, including but not limited to progesterone, estrogen, and testosterone, progestins, corticosteroids, and dehydroepiandrosterone, and any non-protein/non-polypeptide antigens that are listed as international reference standards by the WHO. A partial list of such suitable international reference standards, identified by WHO code in parentheses following the substance, includes vitamin B12 (WHO 81.563), folate (WHO 95/528), homocystein, transcobalamins, T4/T3, and other substances disclosed in the WHO catalog of International Biological Reference Preparations (available at the WHO website, for example at page http://www.who.int/bloodproducts/ref_materials/, updated Jun. 30, 2005), which is incorporated herein by reference. The methods and compositions described herein can comprise one or more of the aforementioned WHO reference standards or a mixture containing a reference standard.

Other examples of substances that may function as one, or alternatively as the other, member of a binding pair consisting of analyte binder (capture moiety) and analyte, depending on the application for which an affinity assay is to be designed include drugs of abuse. Drugs of abuse include, for example, the following list of drugs and their metabolites (e.g., metabolites present in blood, in urine, and other biological materials), as well any salts, esters, or ethers, thereof: heroin, morphine, hydromorphone, codeine, oxycodone, hydrocodone, fentanyl, demerol, methadone, darvon, stadol, talwin, paregoric, buprenex; stimulants such as, for example, amphetamines, methamphetamine; methylamphetamine, ethylamphetamine, methylphenidate, ephedrine, pseudoephedrine, ephedra, ma huang, methylenedioxyamphetamine (MDS), phentermine, phenylpropanolamine; amiphenazole, bemigride, benzphetamine, bromatan, chlorphentermine, cropropamide, crothetamide, diethylpropion, dimethylamphetamine, doxapram, ethamivan, fencamfamine, meclofenoxate, methylphenidate, nikethamide, pemoline, pentetrazol, phendimetrazine, phenmetrazine, phentermine, phenylpropanolamine, picrotoxine, pipradol, prolintane, strychnine, synephrine, phencyclidine and analogs such as angel dust, PCP, ketamine; depressants such as, for example, barbiturates, gluthethimide, methaqualone, and meprobamate, methohexital, thiamyl, thiopental, amobarbital, pentobarbital, secobarbital, butalbital, butabarbital, talbutal, and aprobarbital, phenobarbital, mephobarbital; benzodiazepenes such as, for example, estazolam, flurazepam, temazepam, triazolam, midazolam, alprazolam, chlordiazepoxide, clorazepate, diazepam, halazepam, lorazepam, oxazepam, prazepam, quazepam, clonazepam, flunitrazepam; GBH drugs such as gamma hydroxyl butyric acid and gamma butyrolactone; glutethimide, methaqualone, meprobamate, carisoprodol, zolpidem, zaleplon; cannabinoid drugs such as tetrahydracannabinol and analogs; cocaine, 3-4 methylenedioxymethamphetamine (MDMA); hallucinogens such as, for example, mescaline and LSD.

Other examples of substances that may function as one, or alternatively as the other, member of a binding pair consisting of analyte binder (capture moiety) and analyte, depending on the application for which an affinity assay is to be designed include steroids and other drugs associated with performance enhancement, including those commonly encountered in illicit markets, or employed as ergogenic aids, such as, for example, the following compounds and any salts, esters, or ethers thereof: testosterone (including its esters with moieties such as, for example, enanthate, cypionate, and propionate), dihydrotestosterone (DHT), tetrahydrogestrinone, nandrolone, nortestosterone, methenolone, stanozolol, methandrostenolone, methandienone, androstenedione (e.g., 5a-androstan-3,17-dione), androstenediol such as 1-androstenediol (3.beta.,17.beta.-dihydroxy-5.alpha.-androst-1-ene;), 4-androstenediol (3b17b-dihydroxyandrost-4-ene), 5-androstenediol (3b, 17b-dihydroxy-androst-5-ene), androstendiones, such as 1-androstenedione ([5a]-androst-1-en-3,17-dione), 4-androstenedione (androst-4-en-3,17-dione), 5-androstenedione (androst-5-en-3,17-dione), norandrostenedione, 19-norandrostenediol, 19-norandrostenedione, norandrostenediol, dehydroepiandrosterone (DHEA), boldenone, fluoxymesterone, methandriol, methyltestosterone, oxandrolone, oxymetholone, trenbolone, clostebol, dehydrochloromethyltestosterone, dromostanolone, epitrenbolone, gestrinone, mesterolone, methanedienone, methenolone, norethandrolone, oxandrolone, oxymetholone, tetrahydrogestrinone (THG), trenbolone, clenbutorol, and steroids included in the Anabolic Steroid Control Act of 2004 (incorporated herein by reference), including 3b, 17b-dihydroxy-5a-androstane; 3a,17b-dihydroxy-5a-androstane; androstanedione, bolasterone (7a, 17a-dimethyl-17b-hydroxyandrost-4-en-3-one), boldenone (17b-hydroxyandrost-1,4,-diene-3-one), calusterone (7b,17a-dimethyl-17b-hydroxyandrost-4-en-3-one), clostebol (4-chloro-17b-hydroxyandrost-4-en-3-one), dehydrochlormethyltestosterone (4-chloro-17b-hydroxy-17a-methyl-androst-1,4-dien-3-one), 4-dihydrotestosterone (17b-hydroxy-androstan-3-one), drostanolone (17b-hydroxy-2a-methyl-5a-androstan-3-one), ethylestrenol (17a-ethyl-17b-hydroxyestr-4-ene), fluoxymesterone (9-fluoro-17a-methyl-11b, 17b-dihydroxyandrost-4-en-3-one), formebolone (2-formyl-17a-methyl-11a,17b-dihydroxyandrost-1,4-dien-3-one), furazabol (17a-methyl-17b-hydroxyandrostano[2,3-c]urazan), 18a-homo-17b-hydroxyestr-4-en-3-one (13b-ethyl-17b-hydroxygon-4-en-3-one), 4-hydroxytestosterone (4,17b-dihydroxy-androst-4-en-3-one), 4-hydroxy-19-nortestosterone (4,17b-dihydroxyestr-4-en-3-one), estanolone (17a-methyl-17b-hydroxy-5a-androstan-3-one), mesterolone (1a-methyl-17b-hydroxy-[5a]-androstan-3-one), methandienone (17a-methyl-17b-hydroxyandrost-1,4-dien-3-one), methandriol (17a-methyl-3b, 17b-dihydroxyandrost-5-ene), methenolone (1-methyl-17b-hydroxy-5a-androst-1-en-3-one), ethyltestosterone (17a-methyl-17b-hydroxyandrost-4-en-3-one), mibolerone (7a, 17a-dimethyl-17b-hydroxyestr-4-en-3-one), nandrolone (17b-hydroxyestr-4-en-3-one), norandrostenediol, 19-nor-4-androstenediol (3b, 17b-dihydroxyestr-4-ene), 19-nor-4-androstenediol (3a, 17b-dihydroxyestr-4-ene), 19-nor-5-androstenediol (3b, 17b-dihydroxyestr-5-ene), 19-nor-5-androstenediol (3a, 17b-dihydroxyestr-5-ene), norandrostenedione, 19-nor-4-androstenedione (estr-4-en-3,17-dione), 19-nor-5-androstenedione (estr-5-en-3,17-dione), norbolethone (18a-homo-17b-hydroxypregna-4-en-3-one), norclostebol (4-chloro-17b-hydroxyestr-4-en-3-one), norethandrolone (17a-ethyl-17b-hydroxyestr-4-en-3-one), oxandrolone (17a-methyl-17b-hydroxy-2-oxa-[5a]androstan-3-one), oxymesterone (17a-methyl-4,17b-dihydroxyandrost-4-en-3-one), oxymetholone (17a-methyl-2-hydroxymethylene-17b-hydroxy-[5a]-androstan-3-one), stanozolol (17a-methyl-17b-hydroxy-[5a]-androst-2-eno[3,2-c]-pyrazole), stenbolone (17b-hydroxy-2-methyl-[5a]-androst-1-en-3-one), testolactone (13-hydroxy-3-oxo-13,17-secoandrosta-1,4-dien-17-oic acid lactone), 1-testosterone (17b-hydroxy-5a-androst-1-en-3-one), testosterone (17b-hydroxyandrost-4-en-3-one), tetrahydrogestrinone (13b, 17a-diethyl-17b-hydroxygon-4,9,11-trien-3-one), trenbolone (17b-hydroxyestr-4,9,11-trien-3-one).

Other examples of substances that may function as one, or alternatively as the other, member of a binding pair consisting of analyte binder (capture moiety) and analyte, depending on the application for which an affinity assay is to be designed include antibiotics and other drugs administered to animals (including human beings) and whose detection is useful in clinical practice, and whose detection in a biological preparation can be achieved using, for example, an immunoassay. Examples of such drugs include antibiotics such as those listed in the WHO International Biological Reference preparations (available at http://www.who.int/bloodproducts/ref_materials/Ant-Sept05.pdf, updated as of 21 Sep. 2005, incorporated herein by reference). Examples include gentamicin (92/670), streptomycin (76/539), tobramycin (82/510), and vancomycin (50/020).

Any of the features of the various embodiments described herein can be used in conjunction with features described in connection with any other embodiments disclosed. For example, features disclosed in connection with the compositions of the invention can be employed in any methods described herein, etc. Features described in connection with the various or specific embodiments are not to be construed as not suitable in connection with other embodiments disclosed herein unless' such exclusivity is explicitly stated or implicit from the context.

Certain embodiments of the invention are illustrated in the accompanying Figures and Examples, which are provided to illustrate certain embodiments of the invention, and are not meant to impose limitations on the invention.

BRIEF DESCRIPTION OF THE FIGURES

FIG. 1. Human Anti-Mouse Antibodies (HAMA) from the Cisbio Renin III Generation, Rev. 9, Feb. 7, 2007 package insert.

FIG. 2. Limitations of Procedure from the Beckman Coulter Access 25OH Vitamin D Total Assay, Rev. B25377B instructions for use.

FIG. 3. The primary assay failure modes attributed to HAAA or MASI that can falsely elevate, or falsely suppress, assay signal response and result in erroneous results.

REFERENCES

Figure 4:
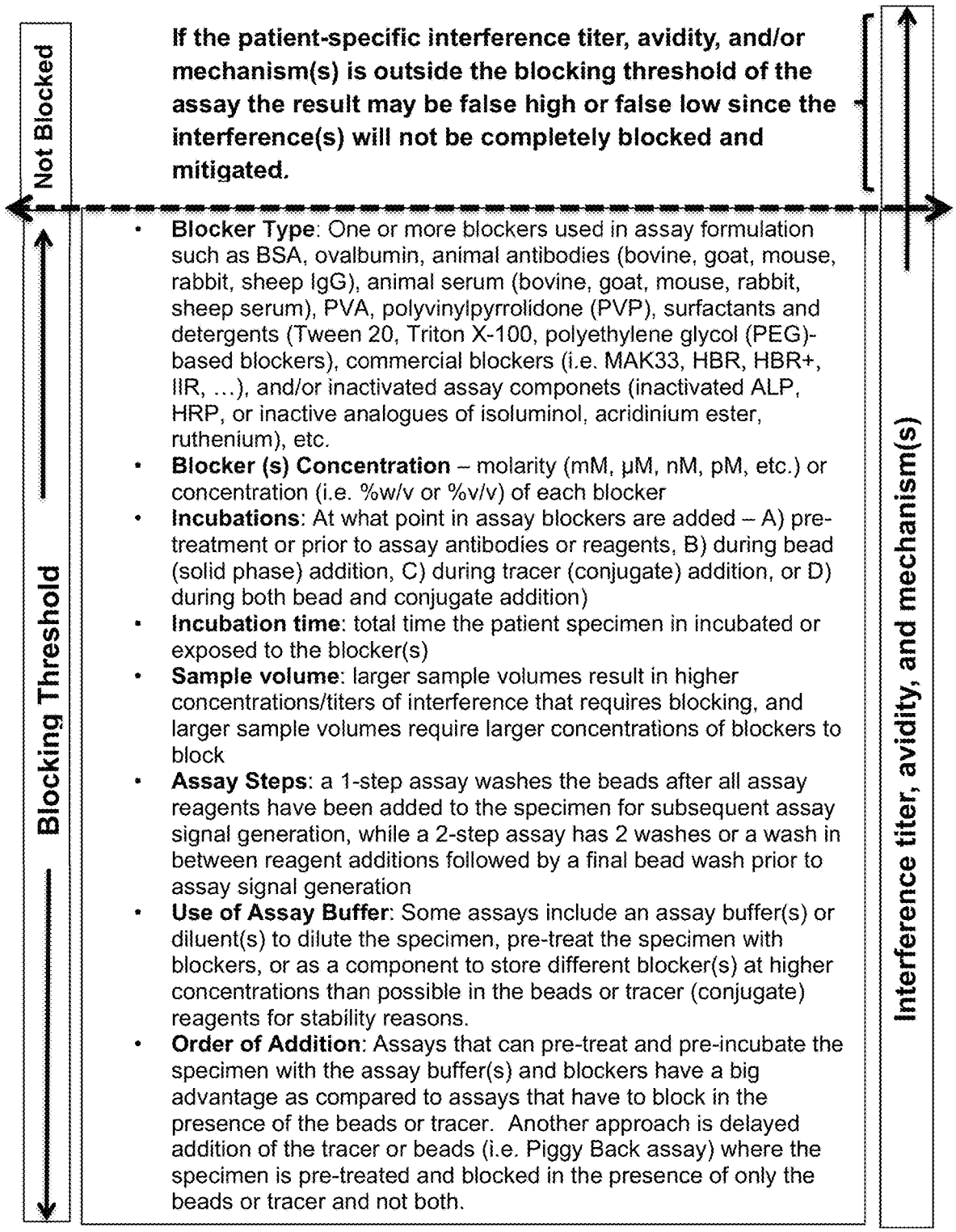
FIG. 4. The ability of an assay to mitigate patient-specific interference regardless of the titer, avidity, and mechanism is the Assay Blocking Threshold (ABT).
Figure 5:
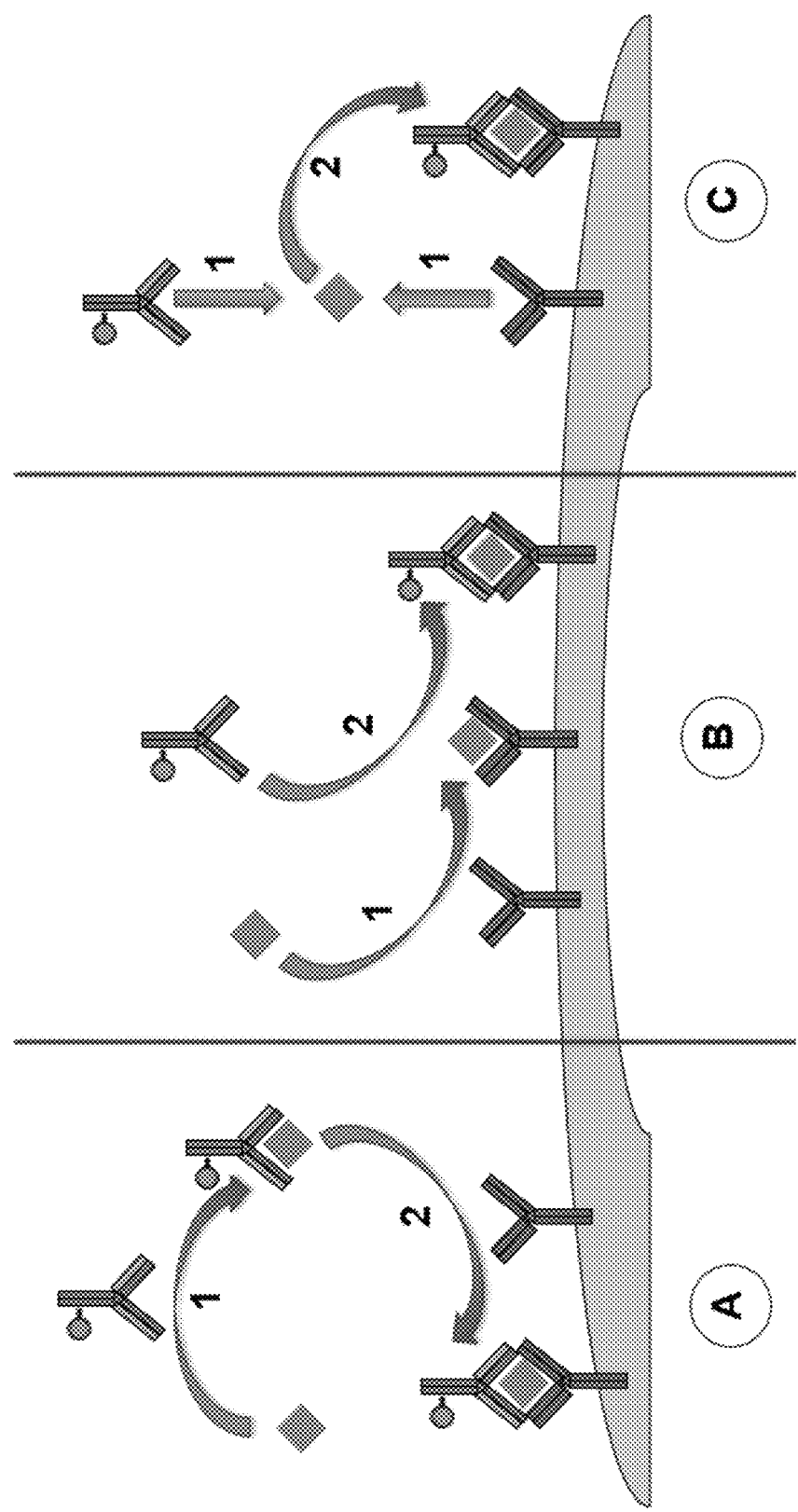
FIG. 5. In a double antibody sandwich assay, a) the conjugate binds antigen first followed by capture antibody; b) the capture antibody binds antigen first followed by conjugate; or c) both the conjugate and capture antibody bind antigen at the same time.
Figure 6:
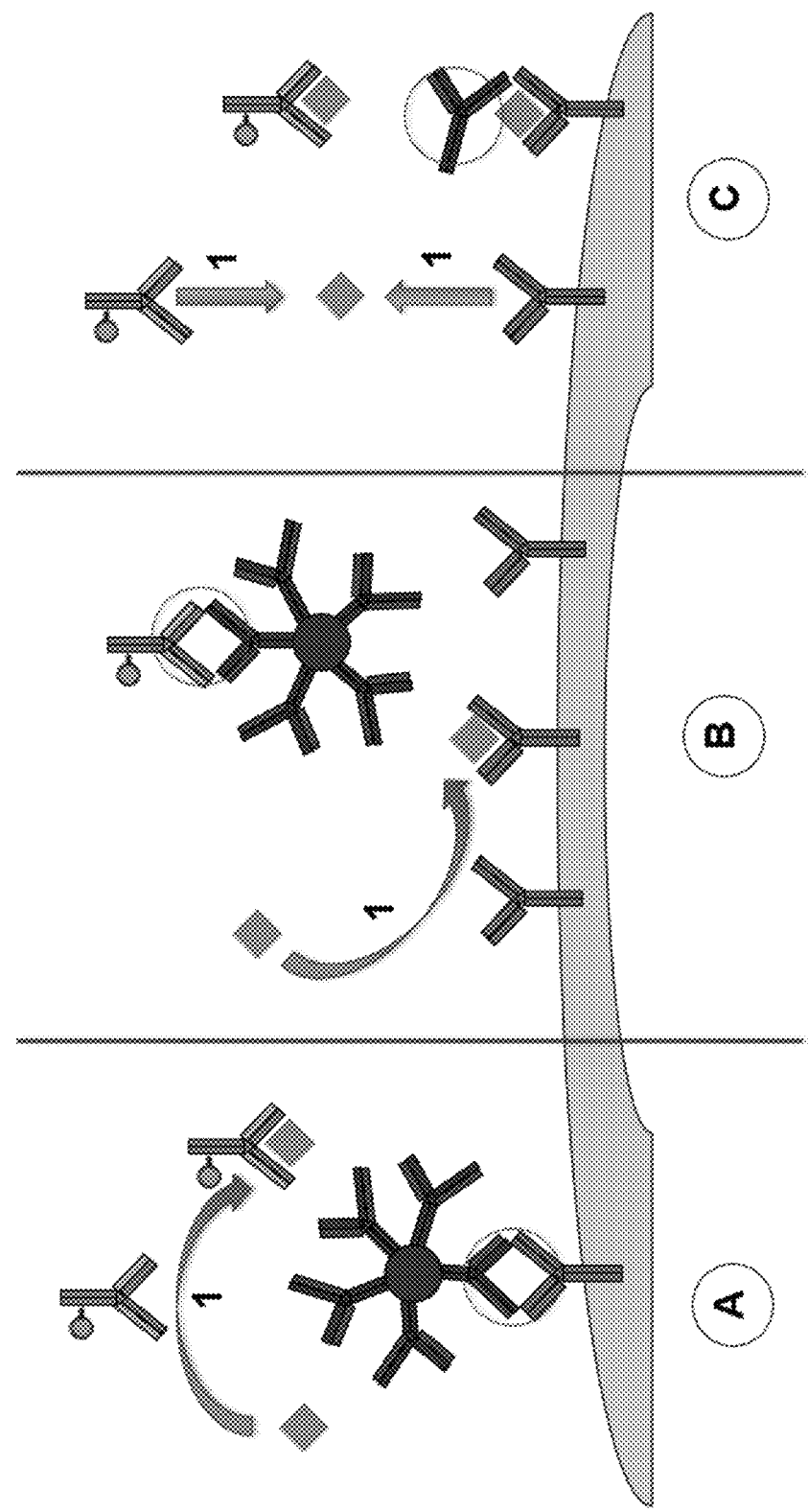
FIG. 6. Human anti-animal (HAAA) interference in a double antibody sandwich assay can result in conjugate steric hindrance and a false low signal if, a) HAAA IgM binds capture antibody and interferes with antigen capture and conjugate binding to the solid phase; b) HAAA IgM binds conjugate and interferes with conjugate antigen binding as well as binding to the solid phase, or c) both conjugate and capture antibody bind antigen but HAAA IgG interferes with subsequent sandwich formation.
Figure 7:
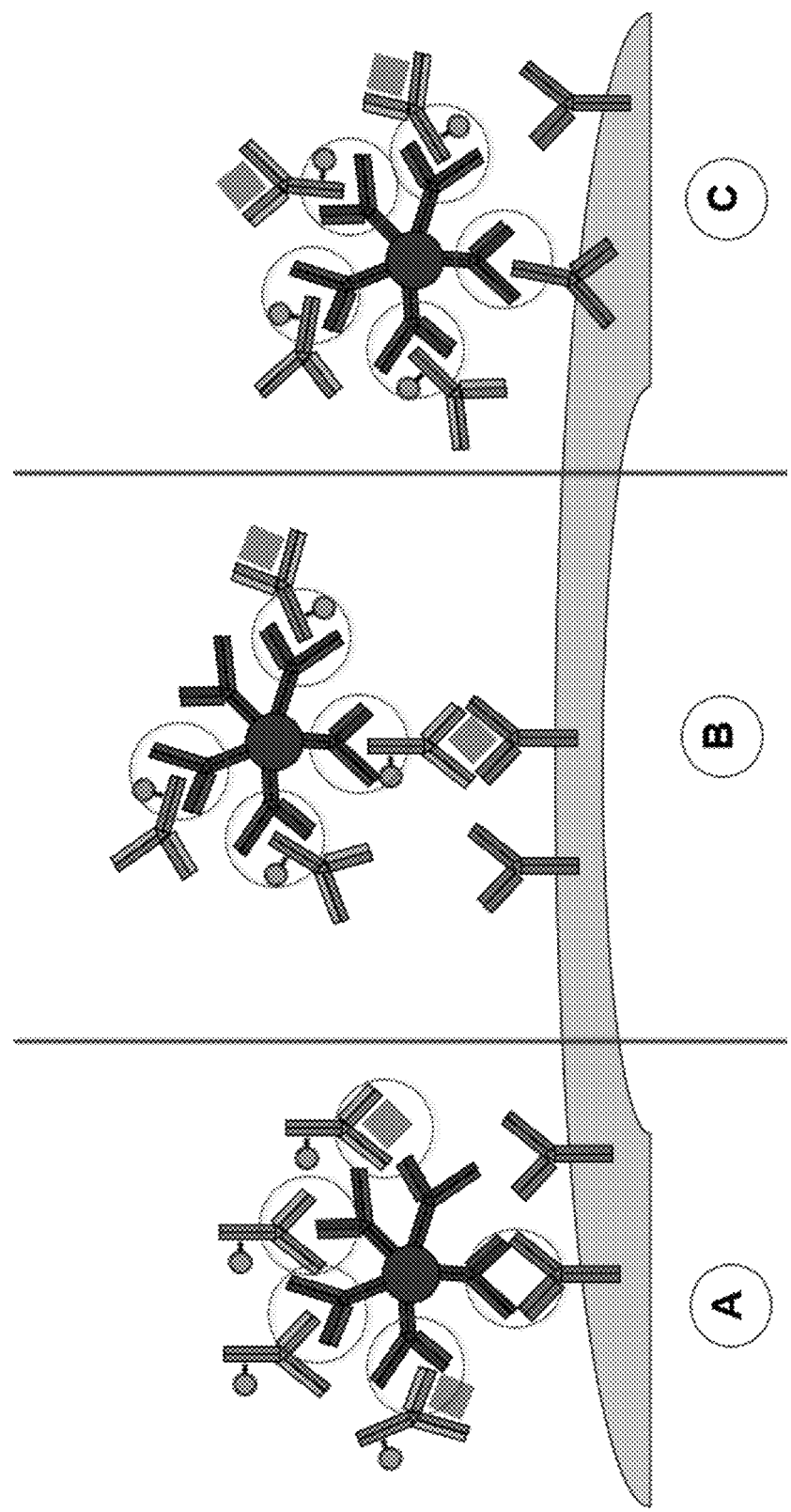
FIG. 7. HAAA interference in a double antibody sandwich assay can result in conjugate bridging and a false high signal if, a) HAAA IgM binds Fab or species specific epitope(s) on both capture antibody and conjugate resulting in excess conjugate binding; b) HAAA IgM binds the Fc portion of conjugate and results in excess conjugate binding; or c) HAAA IgM binds the Fc portion of both capture antibody and conjugate and results in excess conjugate binding.
Figure 8:
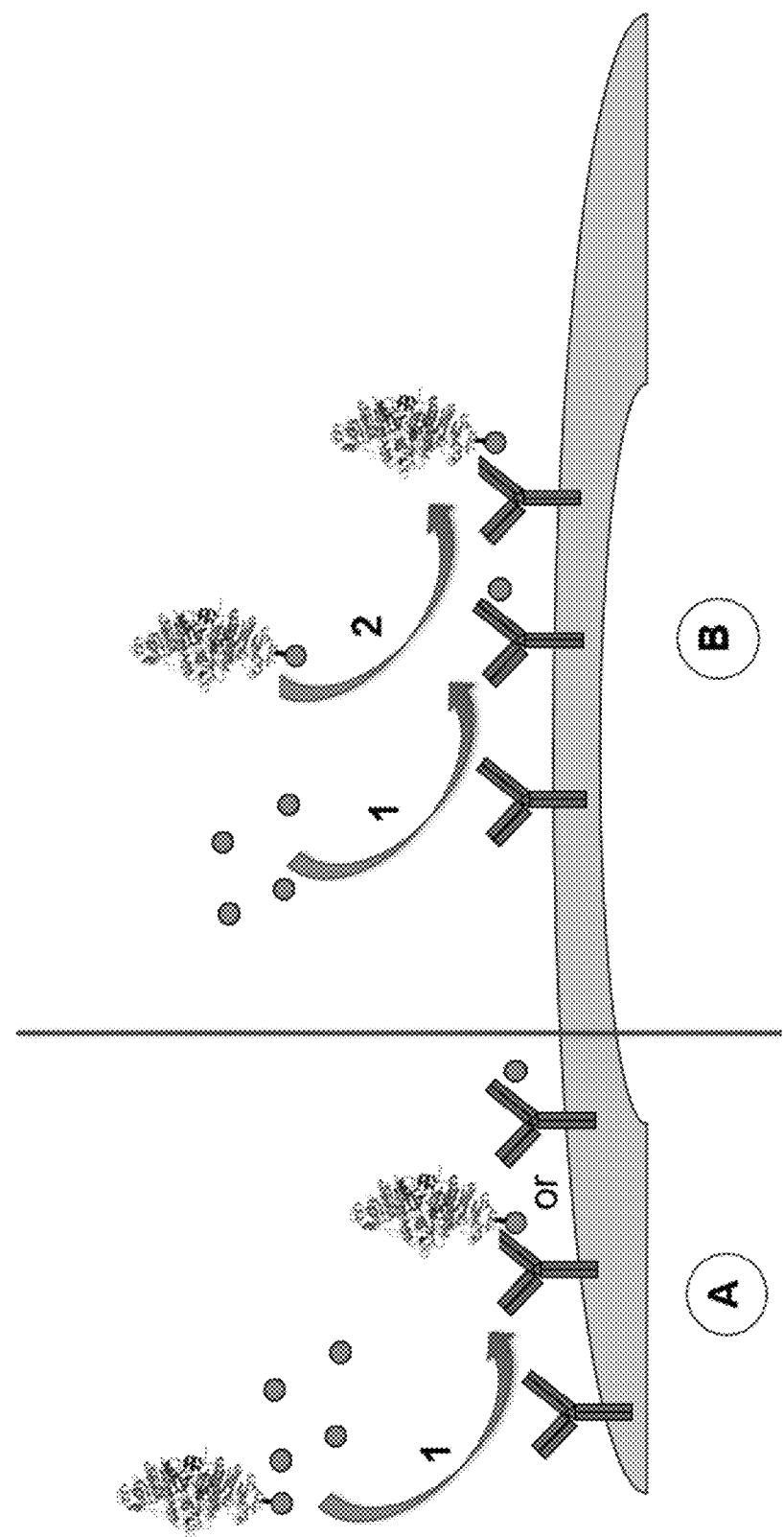
FIG. 8. In a competitive inhibition assay, a) the conjugate and antigen compete for capture antibody (true competition); or b) the antigen binds to capture antibody in the first incubation, and a molar excess of conjugate is added in the second incubation to bind to capture antibody (backfill or piggyback).
Figure 9:
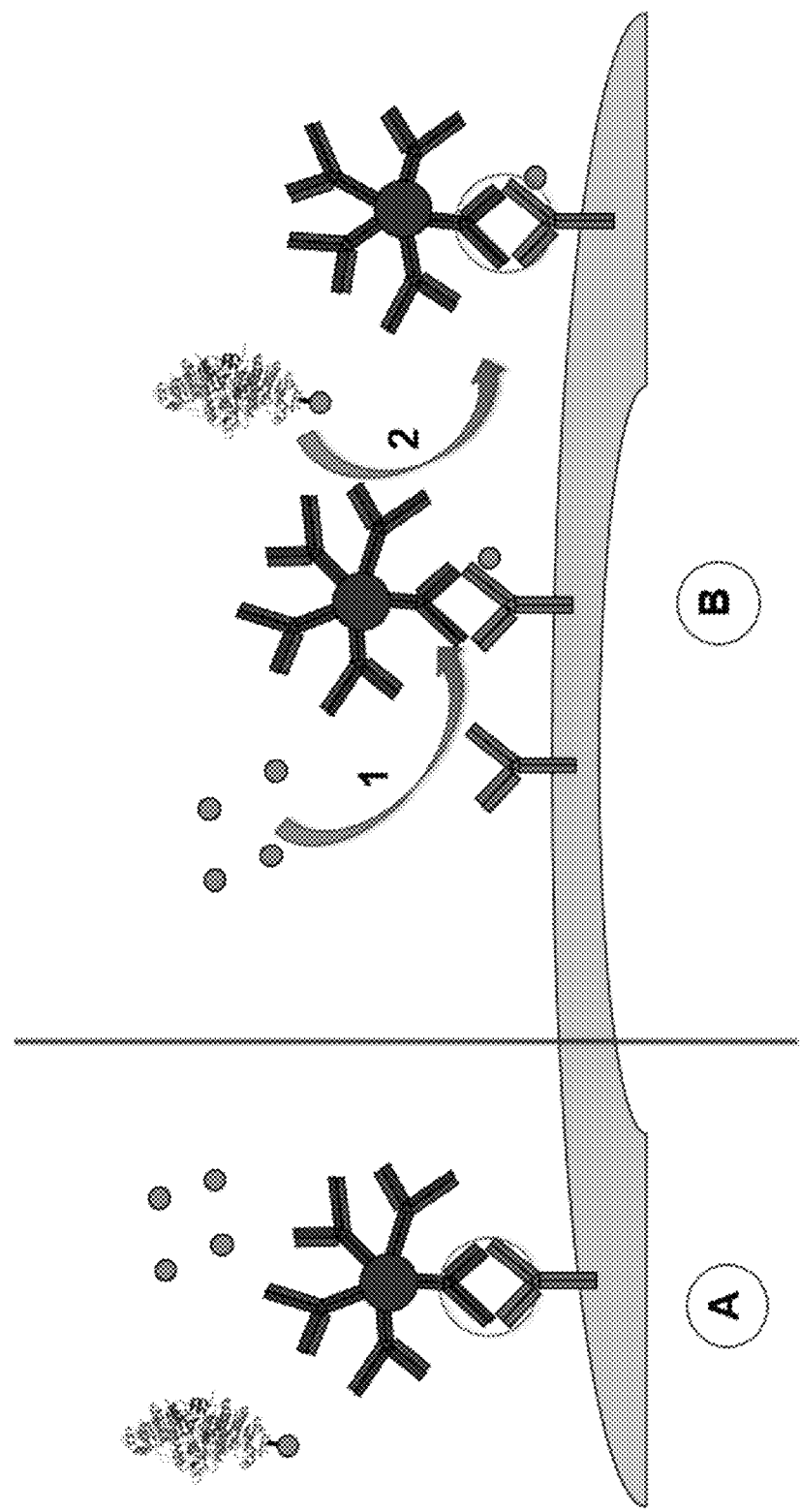
FIG. 9. HAAA interference in a competitive inhibition assay can result in conjugate steric hindrance and a false low signal if, a) HAAA IgM binds capture antibody and interferes with conjugate binding to the solid phase, or b) HAAA IgM binds capture antibody during the first assay incubation and interferes with the conjugate binding during the second assay incubation.
Figure 10:
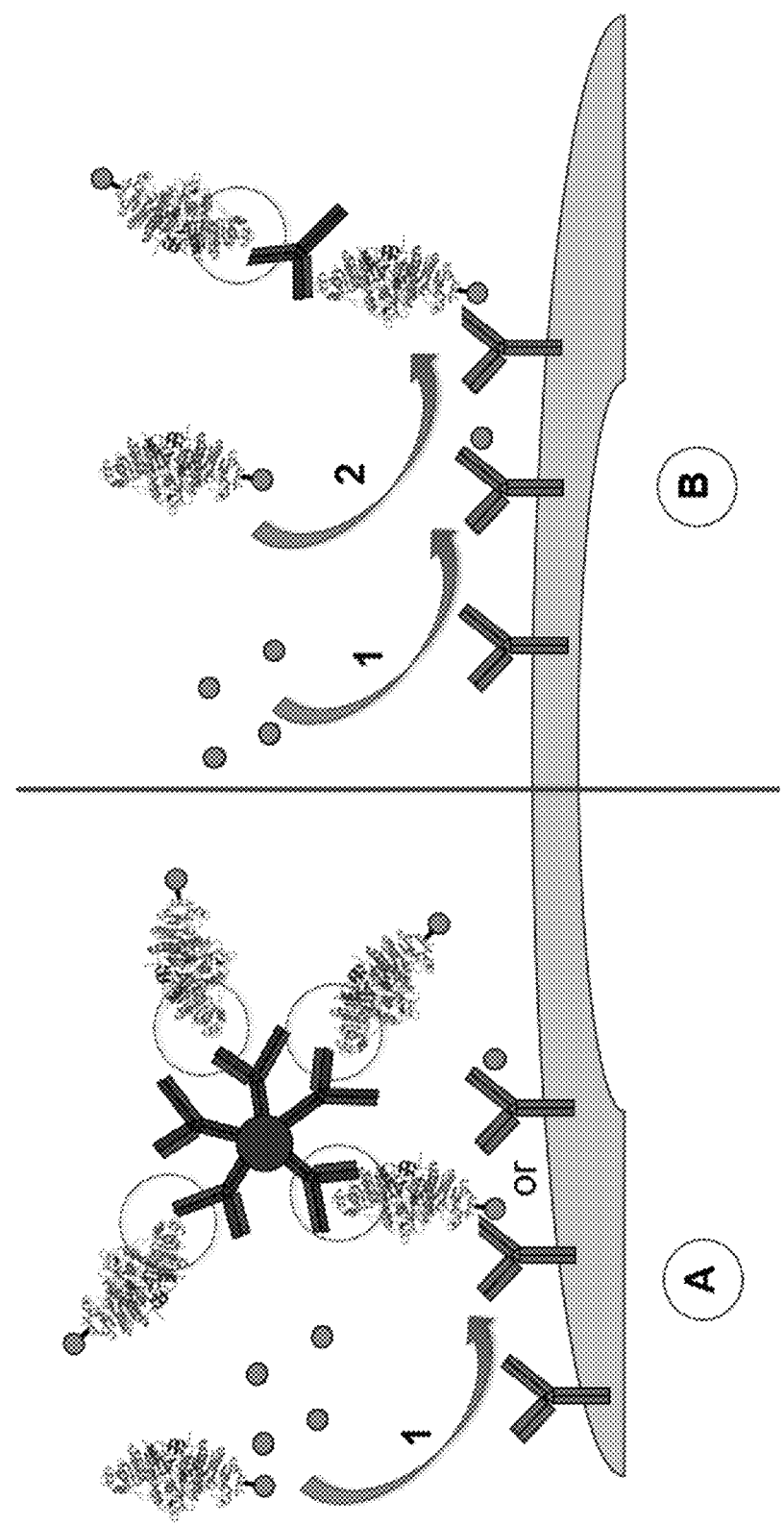
FIG. 10. HAAA interference in a competitive inhibition assay can result in conjugate bridging and a false high signal if, a) HAAA IgM binds conjugate bound to the capture antibody as well as additional conjugate; or b) HAAA IgG binds conjugate bound to the capture antibody in the back fill assay incubation as well as additional conjugate.
Figure 11:
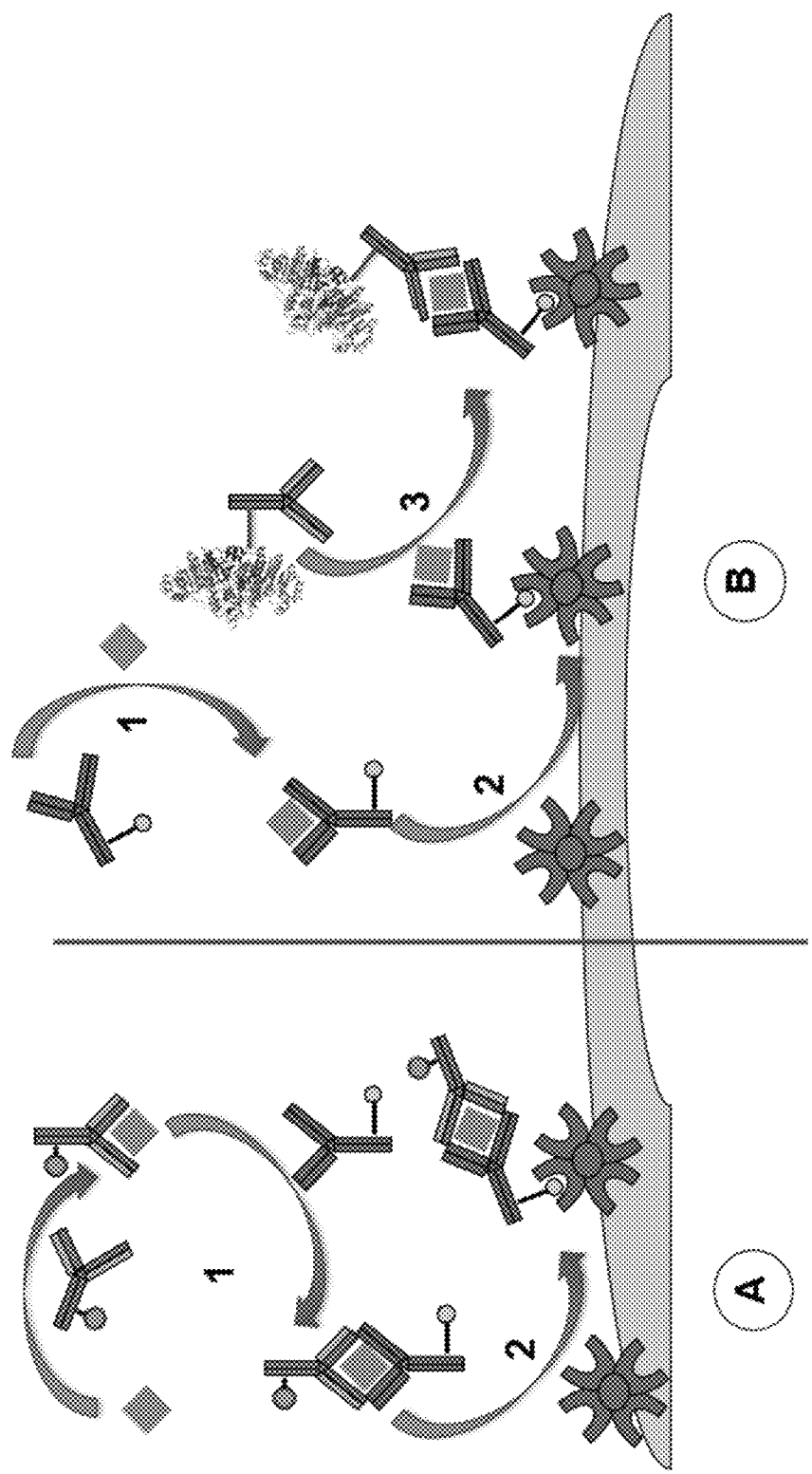
FIG. 11. In a delayed capture assay, a) the conjugate and capture antibody bind antigen and form a solution-based sandwich, and a SAv coated solid phase binds to the biotin tag on the capture antibody, or b) the capture antibody binds antigen, a SAv coated solid phase binds to the biotin tag on the capture antibody, and Conjugate forms a sandwich with the capture antibody-antigen complex.
Figure 12:
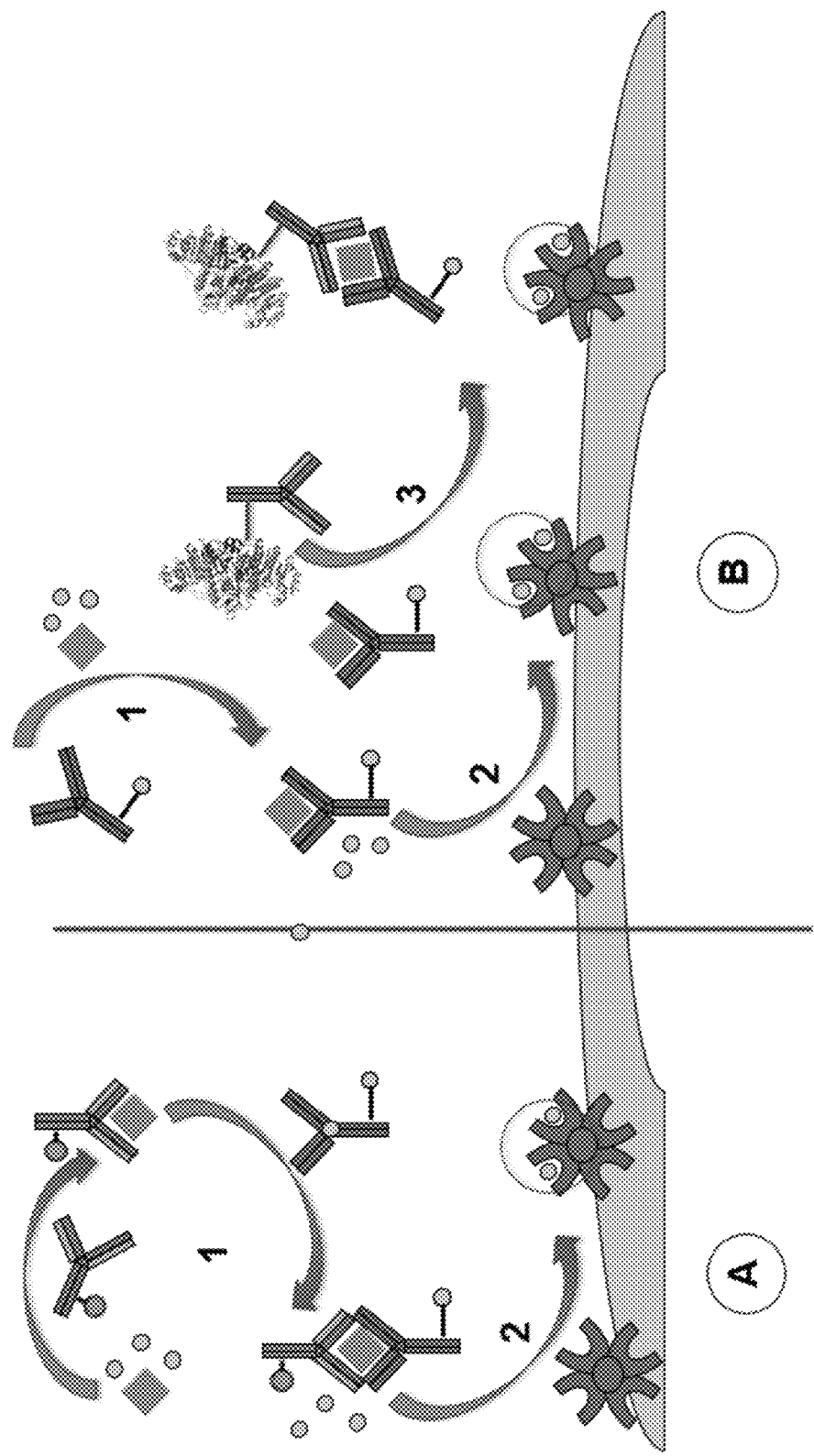
FIG. 12. Two different ways MASI can result in competition for the tag labeled capture antibody and a false low assay signal response in a delayed capture assay, a) free biotin in the sample binds to SAv biotin binding sites and competes for binding of the biotin labeled capture antibody and sandwich complex; b) free biotin in the sample binds to SAv biotin binding sites and competes for binding of the biotin labeled capture antibody prior to the final assay incubation and conjugate addition.
Figure 13:
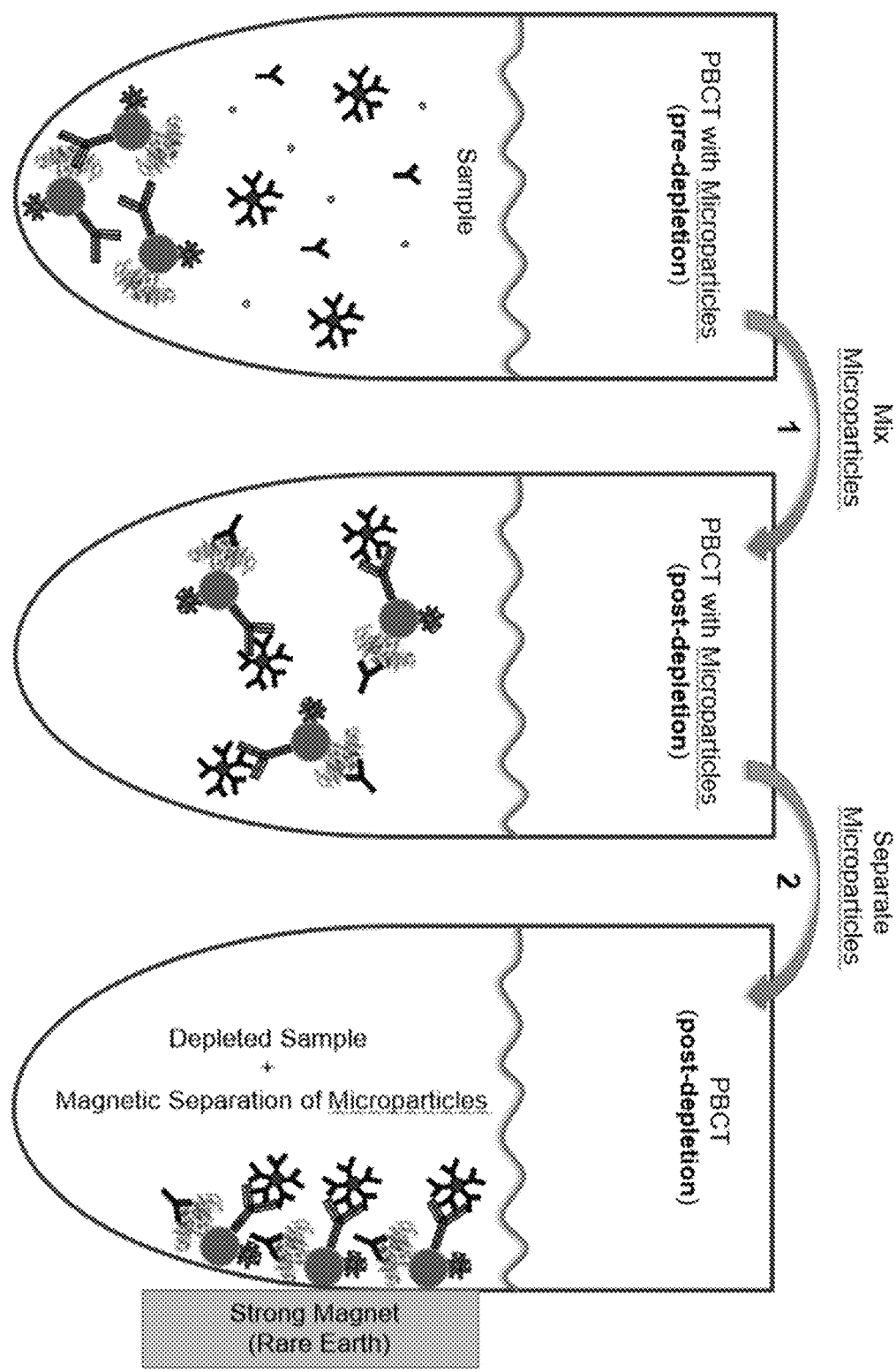
FIG. 13. A plurality of microparticles coated with Mab, ALP and SAv are lyophilized inside the PBCT. When blood is collected in the PBCT and mixed, the microparticles are resuspended and dispersed in the sample. The binders, binding partners and capture moieties coated on the microparticles bind and deplete anti-Mab IgM, anti-ALP IgG, and free biotin interference. Finally, the microparticles are separated and sequestered from the sample using a magnet.
Figure 14:
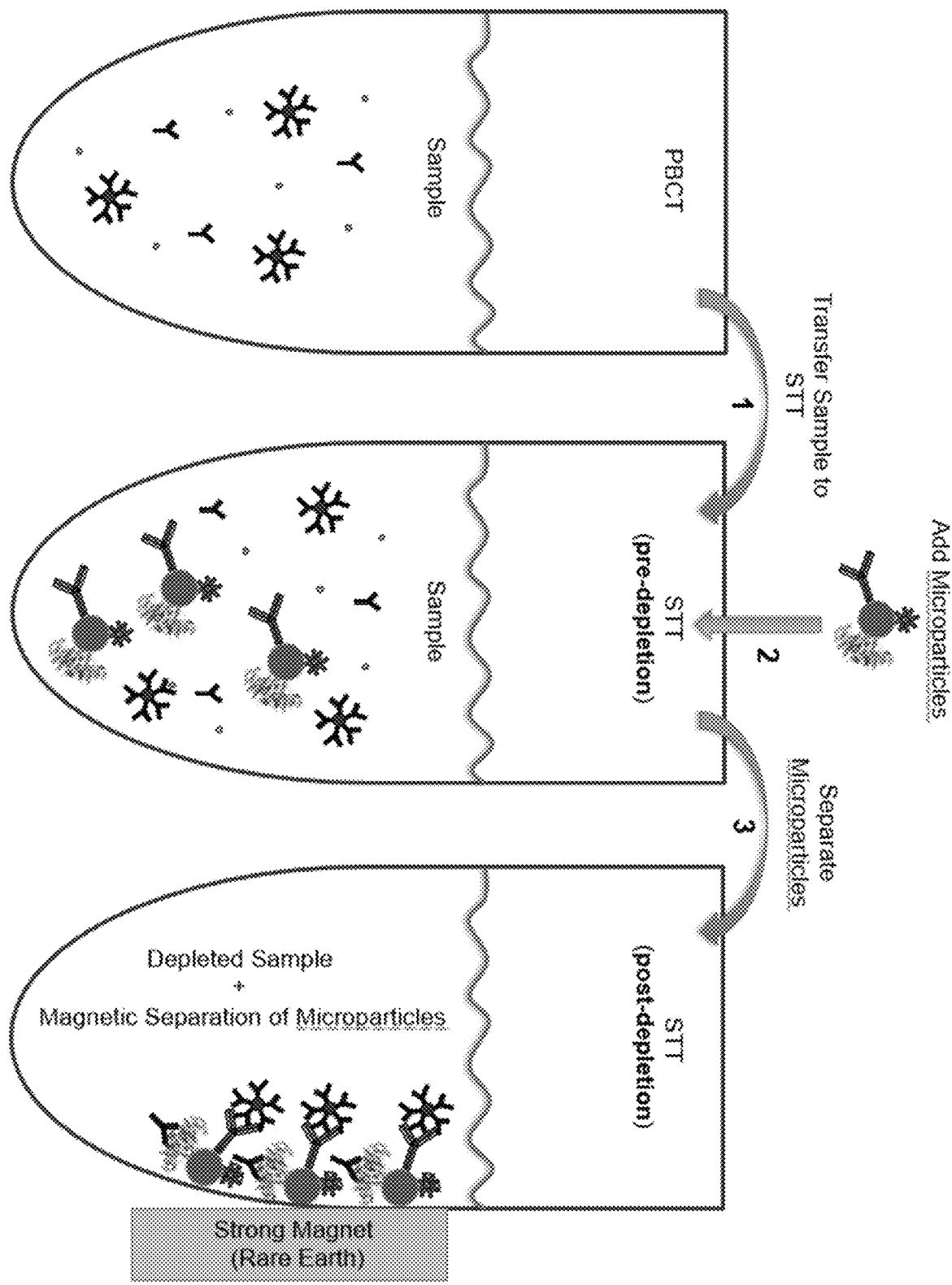
FIG. 14. Sample is aspirated from the PBCT and dispensed into the STT. A plurality of microparticles coated with Mab, ALP and SAv are added to the STT to bind and deplete anti-Mab IgM, anti-ALP IgG, and free biotin interference. Finally, the microparticles are separated and sequestered from the sample using a magnet.
Figure 15:
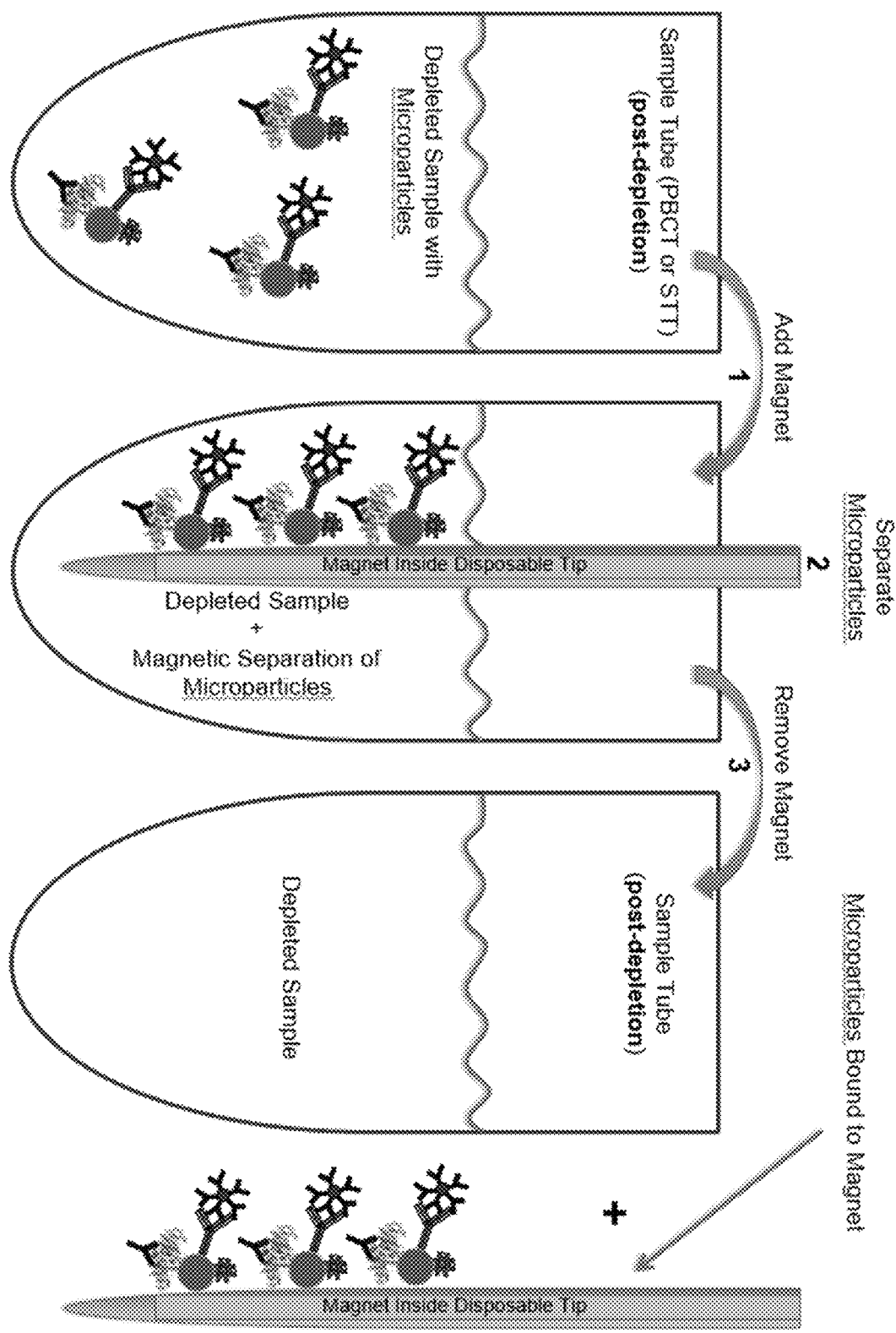
FIG. 15. A plurality of microparticles coated with Mab, ALP and SAv have captured and depleted anti-Mab IgM, anti-ALP IgG, and free biotin interference. A pipette tip and magnetic are used to capture the microparticles. Finally, the pipette tip and microparticles are removed from the sample and discarded.

1. Soldo J, Sackrison J L. Binding Surfaces for Affinity Assays. U.S. Pat. No. 8,518,714, Aug. 27, 2013; EP2069790 (B1), Apr. 29, 2015; HK1129462 (A1), Oct. 30, 2015.
2. Howerton D, Anderson N, Bosse D, Granade S, Westbrook G. Survey Findings from Testing Sites Holding a Certificate of Waiver Under the Clinical Laboratory Improvement Amendments of 1988 and Recommendations for Promoting Quality Testing. MMWR, Recommendations and Reports, Nov. 11, 2005; 54(RR13): 1-25, http://www.cdc.gov/mmwr/preview/mmwrhtml/rr5413a1.htm.

3. Marketsandmarkets.com. *Immunoassay Market [Technology (Enzyme, Fluorescent, Chemiluminescence, Radioimmunoassay), Analyzers & Reagents, Applications (Infectious Diseases, Cancer, Endocrinology, Cardiology), End Users (Hospitals, Laboratory, Academics)]—Global Forecast to 2018*. Markets And Markets, October 2013; Report Code: BT 1653, http://www.marketsandmarkets.com/Market-Reports/immunoassay-market-436.html.

4. Boscato L M, Stuart M C. *Heterophilic antibodies: a problem for all immunoassays*. Clin Chem, 1988; 34(1): 27-33.

5. Kroll M H, Elin R J. *Interference with clinical laboratory analyses*. Clin Chem, 1994; 40(11 Pt 1): 1996-2005. Review. Erratum in: Clin Chem, 1995; 41(5): 770

6. Kricka L J. *Human Anti-Animal Antibody Interferences in Immunological Assays*. Clin Chem, 1999; 45(7): 942-956.

7. Sztefko K. *Interferences in immunoassay*. Przegl Lek, 2002; 59(6): 477-480.

8. Tate J, Ward G. *Interferences in Immunoassay*. Clin Biochem Rev, 2004; 25(2): 105-120.

9. Chiu N H L and Christopoulos T K. Advances in Immunoassay Technology. ISBN 978-953-51-0440-7; Publisher: InTech, March 2012; Schiettecatte J, Anckaert E, Smitz J. *Interferences in Immunoassays*. Chapter 3: 45-62.

10. Kricka L J. *Interferences in immunoassay—still a threat*. Clin Chem, 2000; 46(8 Pt 1): 1037-1038.

11. Ismail A A, Barth J H. *Wrong biochemistry results*. BMJ, 2001; 323(7315): 705-706.

12. Dietrich C G, Stiegler H, Gressner A M, Matern S. *Heterophile antibodies, lack of communication and the diagnostic dilemma*. Med Klin (Munich), 2001; 96(9): 539-544.

13. Levinson S S. *Antibody multispecificity in immunoassay interference*. Clin Biochem, 1992; 25(2): 77-87.

14. Ismail A A, Walker P L, Cawood M L, Barth J H. *Interference in immunoassay is an underestimated problem*. Ann Clin Biochem. 2002; 39(Pt 4): 366-373.

15. Sturgeon C M, Viljoen A. *Analytical error and interference in immunoassay: minimizing risk*. Ann Clin Biochem, 2011; 48(Pt 5): 418-432.

16. Bolstad N, Warren D J, Nustad K. *Heterophilic antibody interference in immunometric assays*. Best Pract Res Clin Endocrinol Metab, 2013; 27(5): 647-661.

17. Sanmartin N, Garcia C, Bugier S, Malfuson J V, Chianea D, Renard C, Vest P. *Heterophilic antibodies: be carefull!*. Ann Biol Clin (Paris), 2013; 71(4): 475-480.

18. Yeo K T, Storm C A, Li Y, Jayne J E, Brough T, Quinn-Hall K S, Fitzmaurice T F. *Performance of the enhanced Abbott AxSYM cardiac troponin I reagent in patients with heterophilic antibodies*. Clin Chim Acta, 2000; 292(1, 2): 13-23.

19. Kim W J, Laterza O F, Hock K G, Pierson-Perry J F, Kaminski D M, Mesguich M, Braconnier F, Zimmermann R, Zaninotto M, Plebani M, Hanna A, Cembrowski G S, Scott M G. *Performance of a revised cardiac troponin method that minimizes interferences from heterophilic antibodies*. Clin Chem, 2002; 48(7): 1028-1034.

20. Tate J R. *Troponin revisited 2008: assay performance*. Clin Chem Lab Med, 2008; 46(11): 1489-1500.

21. Lippi G, Aloe R, Meschi T, Borghi L, Cervellin G. *Interference from heterophilic antibodies in troponin testing. Case report and systematic review of the literature*. Clin Chim Acta, 2013; 426: 79-84.

22. Fortgens P H, Omar F. *Cardiac troponin T quantitative assay failure as a result of antibody interference*. Afr J Lab Med. 2013; 2(1), Art. #23, 3 pages.

23. Bonetti A, Monica C, Bonaguri C, Gnocchi C, Russo A, Battistelli L, Musiari L, Pastori P, Novarini A. *Interference by heterophilic antibodies in immunoassays: wrong increase of myoglobin values*. Acta Biomed, 2008; 79(2): 140-143.

24. Holmes E W, Garbincius J, McKenna K M. *Non-linear analytical recovery in the DiaSorin Liaison immunoassay for 25-hydroxy vitamin D*. Clin Chim Acta, 2011; 412: 2355-2356.

25. Cavalier E, Carlisi A, Beckaert A C, Rousselle O, Chapelle J P. *Human anti-animal interference in DiaSorin Liaison total 25(OH)— vitamin D assay: towards the end of a strange story?* Clin Chim Acta, 2012; 413: 527-528.

26. Farrell C, Soldo J, Williams P, Herrmann M. *25-Hydroxyvitmain D testing: challenging the performance of current automated immunoassays*. Clin Chem Lab Med, 2012; 50: 1953-1963.

27. Holmes E W, Garbincius J, McKenna K M. *Analytical Variability Among Methods for the Measurement of 25-Hydroxyvitamin D*. Am J Clin Pathol, 2013; 140: 550-560.

28. Farrell C J, Soldo J, McWhinney B, Bandodkar S, Herrmann M. *Impact of assay design on test performance: lessons learned from 25-hydroxyvitamin D*. Clin Chem Lab Med, 2014; 52(11): 1579-87.

29. Vladutiu A O, Sulewski J M, Pudlak K A, Stull C G. *Heterophilic antibodies interfering with radioimmunoassay. A false-positive pregnancy test*. JAMA, 1982; 248 (19): 2489-2490.

30. Butler S A, Cole L A. *Use of Heterophilic Antibody Blocking Agent (HBT) in Reducing False Positive hCG Results*. Clin Chem, 2001; 47(7): 1332-1333.

31. Webster R, Fahie-Wilson M, Barker P, Chatterjee V K, Halsall D J. *Immunoglobulin interference in serum follicle-stimulating hormone assays: autoimmune and heterophilic antibody interference*. Ann Clin Biochem, 2010; 47(Pt 4): 386-389.

32. Todd D J, Knowlton N, Amato M, Frank M B, Schur P H, Izmailova E S, Roubenoff R, Shadick N A, Weinblatt M E, Centola M, Lee D M. *Erroneous augmentation of multiplex assay measurements in patients with rheumatoid arthritis due to heterophilic binding by serum rheumatoid factor*. Arthritis Rheum, 2011; 63(4): 894-903.

33. Kragstrup T W, Vorup-Jensen T, Deleuran B, Hvid M. *A simple set of validation steps identifies and removes false results in a sandwich enzyme-linked immunosorbent assay caused by anti-animal IgG antibodies in plasma from arthritis patients*. Springerplus, 2013; 2(1): 263.

34. DeForge L E, Loyet K M, Delarosa D, Chinn J, Zamanian F, Chuntharapai A, Lee J, Hass P, Wei N, Townsend M J, Wang J, Wong W L. *Evaluation of heterophilic antibody blocking agents in reducing false positive interference in immunoassays for IL-17AA, IL-17FF, and IL-17AF*. J Immunol Methods, 2010; 362(1, 2): 70-81.

35. Buijs M M, Gorgets J P, Endert E. *Interference by antiruthenium antibodies in the Roche thyroid-stimulating hormone assay*. Ann Clin Biochem, 2011; 48(Pt 3): 276-281.

36. Sapin R, Agin A, Gasser F. *Efficacy of a new blocker against anti-ruthenium antibody interference in the Elecsys free triiodothyronine assay*. Clin Chem Lab Med, 2007; 45(3): 416-418.

37. Zaninotto M, Tognon C, Venturini R, Betterle C, and Plebani M. *Interference in thyroid hormones with Roche immunoassays: an unfinished story*. Clin Chem Lab Med, 2014; 52(12): e269-e270.

38. Kwok J S, Chan I H, Chan M H. *Biotin interference on TSH and free thyroid hormone measurement*. Pathology. 2012; 44(3): 278-80.
39. Beltran L, Fahie-Wilson M N, McKenna T J, Kavanagh L, Smith T P. *Serum total prolactin and monomeric prolactin reference intervals determined by precipitation with polyethylene glycol: evaluation and validation on common immunoassay platforms*. Clin Chem, 2008; 54(10): 1673-1681.
40. Lakos G. *Interference in antiphospholipid antibody assays*. Semin Thromb Hemost, 2012; 38(4): 353-359.
41. Preissner C M, Dodge L A, O'Kane D J, Singh R J, and Grebe S K G. *Prevalence of Heterophilic Antibody Interference in Eight Automated Tumor Marker Immunoassays*. Clin Chem, 2005; 51(1): 208-210.
42. Vanderstichele H, Stoops E, Vanmechelen E, Jeromin A. *Potential sources of interference on Abeta immunoassays in biological samples*. Alzheimers Res Ther, 2012; 4(5): 39.
43. Altinier S, Varagnolo M, Zaninotto M, Boccagni P, Plebani M. *Heterophilic antibody interference in a non-endogenous molecule assay: an apparent elevation in the tacrolimus concentration*. Clin Chim Acta, 2009; 402(1, 2): 193-195.
44. Marks V. *False-positive immunoassay results: a multi-center survey of erroneous immunoassay results from assays of 74 analytes in 10 donors from 66 laboratories in seven countries*. Clin Chem, 2002; 48(11): 2008-2016.
45. Bolstad N, Warren D J, Bjerner J, Kravdal G, Schwettmann L, Olsen K H, Rustad P, Nustad K. *Heterophilic antibody interference in commercial immunoassays; a screeninq study usinq paired native and pre-blocked sera*. Clin Chem Lab Med, 2011; 49(12): 2001-2006.
46. Gorovits B, McNally J, Fiorotti C, Leung S. *Protein-based matrix interferences in ligand-binding assays*. Bioanalysis, 2014; 6(8): 1131-1140.
47. Rulander N J, Cardamone D, Senior M, Snyder P J, Master S R. *Interference From Anti-Streptavidin Antibody*. Arch Pathol Lab Med, 2013; 137: 1141-1146.
48. Wijeratne N G, Doery J C, Lu Z X. *Positive and negative interference in immunoassays following biotin ingestion: a pharmacokinetic study*. Pathology, 2012; 44(7): 674-675.
49. Holm B E, Sandhu N, Tronstrøm J, Lydolph M, Trier N H, Houen G. *Species cross-reactivity of rheumatoid factors and implications for immunoassays*. Scand J Clin Lab Invest, 2015; 75(1): 51-63.
50. Bjerner J, Olsen K H, Børmer O P, Nustad K. *Human heterophilic antibodies display specificity for murine IgG subclasses*. Clin Biochem, 2005; 38(5): 465-472.
51. 2014 FDA Class 2 Recalls for the Siemens Centaur BRAHAMS PCT assay (Z-1659-2014), TSH3 Ultra assay (Z-1653-2014, Z-1654-2014, Z-1655- 2014), and VitD TOTAL assay (Z-1656-2014, Z-1657-2014, Z-1658-2014), http://www.accessdata.fda.gov/scripts/cdrh/cfdocs/cfRES/res.cfm?id=126653.
52. Xu R N, Fan L, Rieser M J, El-Shourbagy T A. *Recent advances in hiqh-throuqhput quantitative bioanalysis by LC-MS/MS*. JPBA, 2007; 44(2): 342-355.
53. Zheng N, Jiang H, Zeng J. *Current advances and strategies towards fully automated sample preparation for regulated LC-MS/MS bioanalysis*. Bioanalysis, 2014; 6(18): 2441-2459.
54. Bylda C, Thiele R, Kobold U, Volmer D A. *Recent advances in sample preparation techniques to overcome difficulties encountered during quantitative analysis of small molecules from biofluids using LC-MS/MS*. Analyst, 2014; 139(10): 2265-2276.

What is claimed is:

1. A method of depleting heterophilic sample interferences from a sample prior to a diagnostic test by preanalytical processing comprising:
    a) combining a microparticle comprising a microparticulate binding surface with a sample in a collection or transfer tube or device;
    b) mixing the sample with the microparticulate binding surface;
    c) incubating the microparticulate binding surface with the sample to bind and capture the heterophilic interferences and interference mechanisms to the microparticulate binding surface; and then
    d) separating, removing, or eliminating the microparticulate binding surface from the sample to prepare an essentially microparticulate binding surface-free sample supernatant prior to the diagnostic test;
  wherein the microparticulate binding surface comprises:
    i) a microparticle support surface;
    ii) a binder, binding partner, capture moiety or combinations thereof coupled directly to the support surface; the binder, binding partner, or capture moiety is selected from the group consisting of biotin-binding proteins; streptavidin; neutravidin; avidin; biotin-binding fragments of streptavidin; biotin-binding fragments of neutravidin; biotin-binding fragments of avidin; alkaline phosphatase (ALP); horse radish peroxidase (HRP); luminol; isoluminol; ruthenium; acridinium; fluorescein; N-(4-aminobutyl)-N-ethyl-isoluminol (ABEI); biotin; anti-ALP IgG; anti-fluorescein antibody; bovine, goat, mouse, rabbit, sheep, horse, pig, or donkey polyclonal antibodies to target human anti-animal antibodies (HAAA); and mouse IgG, polymerized mouse IgG, Fc fragment of mouse IgG, Fab fragment of mouse IgG, or F(ab')2 fragment of mouse IgG to target human anti-mouse antibodies (HAMA); and
    iii) a binding surface that is blocked with a triblock copolymer, wherein the triblock copolymer is Pluronic F108, Pluronic F127 or Pluronic F68; and whereby the heterophilic sample interference is depleted to within its Assay Blocking Threshold.

2. The method of claim 1, wherein step a) comprises adding two or more microparticulate binding surfaces to the sample, the microparticulate binding surfaces containing different binders, binding partners or capture moieties, thereby targeting more than one interference or interference mechanism in the sample.

3. The method of claim 1, wherein the microparticles are present in a primary blood collection tube (PBCT); a secondary transfer tube (SST), a 24-hour urine collection device; a saliva collection tube; a blood spot filter paper; a collection tube or device for stool or seminal fluid; a light green top or green top plasma separator tube (PST) containing sodium heparin, lithium heparin or ammonium heparin; a light blue top tube containing sodium citrate, citrate, theophylline, adenosine, or dipyridamole (CTAD); a red top tube for serology or immunohematology for the collection of serum in a glass (no additives) or plastic tube (contains clot activators); a red top tube for chemistry for the collection of serum in a glass (no additives) or plastic tube (contains clot activators); a purple lavender top tube containing EDTA K2, EDTA K3, liquid EDTA solution, or EDTA K2/gel tubes for testing plasma in molecular diagnostics and viral load detection; a pink top tube for blood bank EDTA; a gray top tube containing potassium oxalate and sodium fluoride, sodium fluoride/EDTA, or sodium fluoride (no anticoagulant); a yellow top tube containing ACD solution A or ACD solution B; a royal blue top (serum, no additive or sodium heparin); or a white top tube; prior to sample collection or transfer.

4. The method of claim 3; wherein the PBCT is used for short turn-around time (STAT) diagnostic tests, ambulatory tests, lateral flow tests, point of care (PoC) tests, molecular diagnostic tests, HPLC, MS, LCMS, LC-MS/MS, radioimmunoassay (RIA), enzyme-linked immunoassay (ELISA), chemiluminescence immunoassay (CLIA), CLIA and CLIA waived tests, or a diagnostic test used for diagnosis, prognosis, screening, risk assessment, risk stratification, treatment monitoring, or therapeutic drug monitoring.

5. The method of claim 1, wherein the essentially microparticulate binding surface-free sample supernatant contains 0% (w/v) to 1% (w/v) microparticle.

6. The method of claim 1, wherein step d) comprises i) centrifuging at 1000×g or greater for at least 5 minutes to form a pellet of microparticles at the bottom of a centrifuge tube and an essentially microparticle-free sample supernatant; and ii) aspirating the essentially microparticle-free supernatant.

7. The method of claim 1, wherein step d) comprises i) selecting a filter material with a porosity or molecular weight cut-off (MWCO) sufficiently smaller than the diameter of the microparticles such that the microparticles will not pass through the filter; and ii) gravity-, vacuum- or centrifuge-filtering the sample into a collection device such that the filtrate is essentially microparticulate binding surface-free.

8. The method of claim 1, wherein the microparticle is magnetic, paramagnetic, or superparamagnetic and step d) comprises i) using a magnet to form a pellet of microparticles on the sides or bottom of a sample container and form an essentially microparticulate binding surface-free sample supernatant; and ii) aspirating the essentially microparticulate binding surface-free sample supernatant.

9. The method of claim 1, wherein the microparticle is magnetic, paramagnetic, or superparamagnetic and step d) comprises i) inserting a disposable pipette tip, cover or sheath containing a magnet into the sample to collect the microparticles on the surface of the pipette tip, cover or sheath such that the sample supernatant is essentially microparticulate binding surface-free; and ii) aspirating the essentially microparticulate binding surface-free sample supernatant.

10. The method of claim 1, wherein the essentially microparticulate binding surface-free sample supernatant contains 0% (w/v) to 0.1% (w/v) microparticle.

11. The method of claim 1, wherein the essentially microparticulate binding surface-free sample supernatant contains 0% (w/v) to 0.01% (w/v) microparticle.

12. The method of claim 1, wherein the sample is selected from the group consisting of: human serum, animal serum, plasma, blood, whole blood, processed blood, urine, saliva, liquid stool, stool solid, semen, seminal fluid, cells, tissues, biopsy material, DNA, and RNA.

13. The method of claim 1, wherein the interference is selected from the group consisting of: human anti-mouse antibodies (HAMA), human anti-animal antibodies (HAAA), human anti-goat antibodies, human anti-rabbit antibodies, human anti-sheep antibodies, human anti-bovine antibodies, human anti-mouse antibodies, human anti-horse antibodies, human anti-pig antibodies, human anti-donkey antibodies, biotin, anti-ALP IgG, and anti-fluorescein antibody.

14. The method of claim 1, wherein the microparticle support surface comprises a material selected from the group consisting of: ceramic, glass, a polymer, a copolymer, metal, latex, silica, a colloidal metal, gold, silver, alloys, polystyrene, derivatized polystyrene, poly(divinylbenzene), styrene-acylate copolymer, styrene-butadiene copolymer, styrene-divinylbenzene copolymer, poly(styrene-oxyethylene), polymethyl methacrylate, polymethacrylate, polyurethane, polyglutaraldehyde, polyethylene imine, polyvinylpyrrolidone, polyvinyl alcohol, polyacrylic acid, N,N'-methylene bis-acrylamide, polyolefins, polyethylene, polypropylene, polyvinylchloride, polyacrylonitrile, polysulfone, poly(ether sulfone), pyrolized materials, block copolymers, and copolymers of the foregoing, silicones, silica, methylol melamine, a biodegradable polymer, dextran, poly(ethylene glycol)-dextran (PEG-DEX), iron oxide, ferromagnetic iron oxide, $Fe_2O_3$, and $Fe_3O_4$, maghemite, and combinations thereof.

15. The method of claim 1, wherein the microparticle support surface comprises one or more functional groups for covalent attachment of a binder, binding partner, capture moiety or combinations thereof selected from the group consisting of: carboxyl, tosyl, epoxy, amine, sulfhydryl, hydroxyl, ester, maleimide, azide, alkyne, nitrone, alkene, tetrazine, tetrazole, hydrazone, succinimidyl, succinimidyl-6-hydrazine-nicotinamide, N-succinimidyl-4-formylbenzamide, and photoreactive groups.

16. The method of claim 1, wherein the microparticle has a mean diameter of about 0.05 μm to about 3 μm.

17. The method of claim 1, further comprising enriching a biomarker in the essentially microparticulate binding surface-free sample supernatant prior to the diagnostic test comprising a) incubating the essentially microparticulate binding surface-free sample supernatant with a biomarker-targeting microparticle comprising a biomarker-targeting microparticulate binding surface to bind and capture a targeted biomarker to the microparticulate binding surface; b) separating or removing the biomarker-targeting microparticulate binding surface from supernatant; and c) washing the biomarker-targeting microparticulate binding surface to remove non-specific materials.

18. The method of claim 1, wherein the binder, binding partner, or capture moiety is selected from the group consisting of BSA conjugated to isoluminol, BSA conjugated to ruthenium, BSA conjugated to acridinium, BSA conjugated to fluorescein, and BSA conjugated to N-(4-aminobutyl)-N-ethyl-isoluminol (ABEI).

19. The method of claim 1, wherein the binder, binding partner, or capture moiety comprises biotin-binding proteins; streptavidin; neutravidin; avidin; biotin-binding fragments of streptavidin; biotin-binding fragments of neutravidin; biotin-binding fragments of avidin; alkaline phosphatase (ALP); horse radish peroxidase (HRP); luminal, isoluminol; ruthenium; acridinium; fluorescein; N-(4-aminobutyl)-N-ethyl-isoluminol (ABEI); biotin, anti-ALP IgG, or anti-fluorescein antibody.

20. The method of claim 1, wherein the binder, binding partner, or capture moiety comprises bovine, horse, pig, or donkey polyclonal antibodies to target human anti-animal antibodies (HAAA); or polymerized mouse IgG or Fc fragment of mouse IgG, to target human anti-mouse antibodies (HAMA).

21. The method of claim 1, wherein the microparticle comprising the microparticulate binding surface is present in the primary blood collection tube or device with whole blood.

* * * * *